US012754179B2

(12) United States Patent
McKeating et al.

(10) Patent No.: US 12,754,179 B2
(45) Date of Patent: Oct. 6, 2026

(54) VERTICAL FLOW ASSAY DEVICE AND METHOD FOR DETERMINATION OF HEMOGLOBIN CONCENTRATION

(71) Applicant: Google LLC, Mountain View, CA (US)

(72) Inventors: Kristy McKeating, San Francisco, CA (US); Herschel Watkins, Woodacre, CA (US)

(73) Assignee: GOOGLE LLC, Mountain View, CA (US)

( * ) Notice: Subject to any disclaimer, the term of this patent is extended or adjusted under 35 U.S.C. 154(b) by 874 days.

(21) Appl. No.: 18/013,682

(22) PCT Filed: Oct. 19, 2021

(86) PCT No.: PCT/US2021/055575
§ 371 (c)(1),
(2) Date: Dec. 29, 2022

(87) PCT Pub. No.: WO2023/069076
PCT Pub. Date: Apr. 27, 2023

(65) Prior Publication Data

US 2024/0094190 A1 Mar. 21, 2024

(51) Int. Cl.
*G01N 33/49* (2006.01)
*B01L 3/00* (2006.01)
*G01N 33/72* (2006.01)

(52) U.S. Cl.
CPC .......... *G01N 33/491* (2013.01); *B01L 3/5023* (2013.01); *G01N 33/726* (2013.01);
(Continued)

(58) Field of Classification Search
CPC .. G01N 33/491; G01N 33/726; G01N 33/721; G01N 33/52; G01N 33/487;
(Continued)

(56) References Cited

U.S. PATENT DOCUMENTS 5,580,744 A * 12/1996 Zweig .................... G01N 33/86 530/381
6,287,867 B1 9/2001 Harttig et al.
(Continued)

FOREIGN PATENT DOCUMENTS

CN 101501497 8/2009
CN 110199186 9/2019

OTHER PUBLICATIONS

International Search Report for Application No. PCT/ US2021/ 055575, mailed on Jun. 29, 2022, 6 pages.
(Continued)

*Primary Examiner* — Dennis White
(74) *Attorney, Agent, or Firm* — DORITY & MANNING, P.A.

(57) ABSTRACT

The present disclosure provides an assay device for determining a concentration of hemoglobin in a sample. The device includes a separation membrane containing a cell lysing reagent that is present on the separation membrane in an amount greater than 200 micrograms/square centimeter to less than 675 micrograms/square centimeter. Further, the device includes a downstream detection membrane configured to elicit a quantifiable response in the presence of hemoglobin. The detection membrane includes an asymmetric membrane having a first plurality of pores located towards an upstream side of the detection membrane and a second plurality of pores located towards a downstream side of the detection membrane. The first plurality of pores are larger than the second plurality of pores. The present disclosure also provides methods for using a vertical flow assay device to lyse the red blood cells in the sample to quantify the level of hemoglobin present via reflectance spectroscopy.

20 Claims, 17 Drawing Sheets

(52) U.S. Cl.
CPC ... *B01L 2200/0652* (2013.01); *B01L 2200/16* (2013.01); *B01L 2300/0681* (2013.01); *B01L 2400/0406* (2013.01)

(58) Field of Classification Search
CPC ........ G01N 21/25; G01N 21/64; G01N 21/78; G01N 27/26; G01N 33/521; B01L 3/5023; B01L 2200/0652; B01L 2200/16; B01L 2300/0681; B01L 2400/0406
See application file for complete search history.

(56) References Cited

U.S. PATENT DOCUMENTS

| | | | | |
|---|---|---|---|---|
| 2004/0156037 | A1 | 8/2004 | Mawhirt et al. | |
| 2012/0264137 | A1* | 10/2012 | Vanjari .............. | G01N 33/5436 435/7.1 |
| 2017/0030932 | A1* | 2/2017 | Ledden ............. | B01L 3/502753 |

OTHER PUBLICATIONS

International Preliminary Report on Patentability for Application No. PCT/US2021/055575, mailed May 2, 2024, 7 pages.

Chinese Search Report Corresponding to Application No. 2021800463868 on Jul. 15, 2026.

Joung et al., “Paper-based Multiplexed Vertical Flow Assay for Point-of-Care Testing”, Lab on a Chip, Jan. 31, 2019, 10 pages.

* cited by examiner

VERTICAL FLOW ASSAY DEVICE AND METHOD FOR DETERMINATION OF HEMOGLOBIN CONCENTRATION

CROSS-REFERENCE TO RELATED APPLICATIONS

The present application is based upon and claims the right of priority under 35 U.S.C. § 371 to International Application No. PCT/US2021/055575, filed on Oct. 19, 2021, which is incorporated by reference herein.

FIELD

The present disclosure relates generally to a point-of-care (POC) testing system that includes an assay device. More particularly, the present disclosure relates to assay devices and methods for determining the concentration of hemoglobin in a blood fluid sample utilizing a vertical flow assay device.

BACKGROUND

Point-of-care (POC) testing refers to performing medical diagnostic tests at the time and place that the patient is being treated. POC testing is advantageous over traditional diagnostic testing where patient samples are sent out to a laboratory for further analysis, because the results of traditional diagnostic tests may not be available for hours, if not days or weeks, making it difficult for a caregiver to assess the proper course of treatment in the interim.

Of particular interest in POC testing is the determination of the level of hemoglobin present in a blood fluid sample, where a low level of hemoglobin may be useful in assessing if a patient is anemic. The most common method of hemoglobin determination is the hemiglobincyanide (HiCN) test, which has been adopted as a reference method by the International Committee for Standardization in Hematology (ICSH). In this test, a person's blood is diluted in a solution containing potassium ferricyanide and potassium cyanide, and the resulting chemical complex is measured using absorbance spectroscopy. However, some major drawbacks of this test include the hazardous nature of the chemicals involved and the laboratory equipment needed to prepare for and run the analysis. These drawbacks make it not feasible to use this test in an at home device.

Further, currently available hemoglobin assay devices for at home use only measure for hemoglobin, while it would be useful to also measure other analytes in combination with hemoglobin. Additionally, many hemoglobin tests utilize the light transmission to determine the level of hemoglobin present, which requires the light source and detector to be placed on opposite sides of the sample to get accurate measurements. For example, the HemoCue® device is a portable instrument that uses milder chemicals in a disposable cuvette that lyse red blood cells in a sample and form a complex with the hemoglobin present, which can be measured using absorbance spectroscopy. The major drawback of this type of device, however, is that such devices are designed to measure hemoglobin alone with no other blood-based analyte. Additionally, the method of analysis is transmission based spectroscopy, which arguably makes the device more limited in its design and use. In particular, transmission spectroscopy can be more error prone than reflectance spectroscopy based on turbidity correction. Transmission spectroscopy for hemoglobin quantification uses two wavelengths: one to measure hemoglobin concentration and the other to correct for sample turbidity. Unfortunately, if there is anything in the sample which absorbs at the second wavelength, the turbidity correction will create erroneous results. Another similar device is the AimStrip® hemoglobin analyzer.

Thus, it would be desirable to have a POC system that can determine an amount of hemoglobin present in a blood fluid sample without the use of harsh chemicals and with an easier to use electronics system, it would also be beneficial to be able to incorporate the hemoglobin assay into a POC system that can also measure for other analytes in the blood fluid sample.

SUMMARY

Aspects and advantages of embodiments of the present disclosure will be set forth in part in the following description, or can be learned from the description, or can be learned through practice of the embodiments.

One example aspect of the present disclosure is directed to an assay device (as part of a POC testing system) for determining a concentration of hemoglobin in a blood fluid sample. The assay device includes a separation membrane and a detection membrane. The separation membrane is coated with a solution containing a cell lysing reagent, and the cell lysing reagent is present in the solution in an amount greater than 0.75 wt. % and less than 2.5 wt. % based on the wet weight of the solution. Further, it should be understood that the cell lysing reagent is present on the separation membrane in an amount greater than 200 micrograms/square centimeter to less than 675 micrograms/square centimeter based on the dry weight of the cell lysing reagent on the separation membrane after the solution has dried on the separation membrane. The detection membrane is located downstream from the separation membrane and is configured to elicit a quantifiable response in the presence of hemoglobin in the blood fluid sample. The quantifiable response corresponds to an amount of hemoglobin present in the blood fluid sample. Further, the detection membrane is asymmetric and has a first plurality of pores located towards an upstream side of the detection membrane (i.e., in an upstream portion of the detection membrane) and a second plurality of pores located towards a downstream side of the detection membrane (i.e., in a downstream portion of the detection membrane). In addition, the first plurality of pores have an average pore size that is larger than an average pore size of the second plurality of pores.

Another aspect of the present disclosure is directed to an in vitro use of the proposed assay device for determining the concentration of hemoglobin present in the blood fluid sample.

Yet another aspect of the present disclosure is directed to a use of the assay device in a diagnostic method for determining the concentration of hemoglobin present in the blood fluid sample.

Still another aspect of the present disclosure is directed to a method of fabricating an assay device for analyzing a blood fluid sample. The method includes, in no particular order, the steps of: coating a solution containing a cell lysing reagent onto to a separation membrane, wherein the cell lysing reagent is present in the solution in an amount greater than 0.75 wt. % and less than 2.5 wt. % based on the wet weight of the solution; allowing the solution to dry on the separation membrane, where, for example, the cell lysing reagent is present in an amount greater than 200 micrograms/square centimeter to less than 675 micrograms/square centimeter based on the dry weight of the cell lysing reagent after the cell lysing reagent has dried on the separation membrane; and positioning a detection membrane downstream from the separation membrane. The detection membrane is configured to elicit a quantifiable response in the presence of hemoglobin in the blood fluid sample, and the quantifiable response corresponds to an amount of hemoglobin present in the blood fluid sample. Further, the detection membrane is asymmetric and has a first plurality of pores located towards an upstream side of the detection membrane and a second plurality of pores located towards a downstream side of the detection membrane. In addition, the first plurality of pores have an average pore size that is larger than an average pore size of the second plurality of pores.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which.

Figure 1:
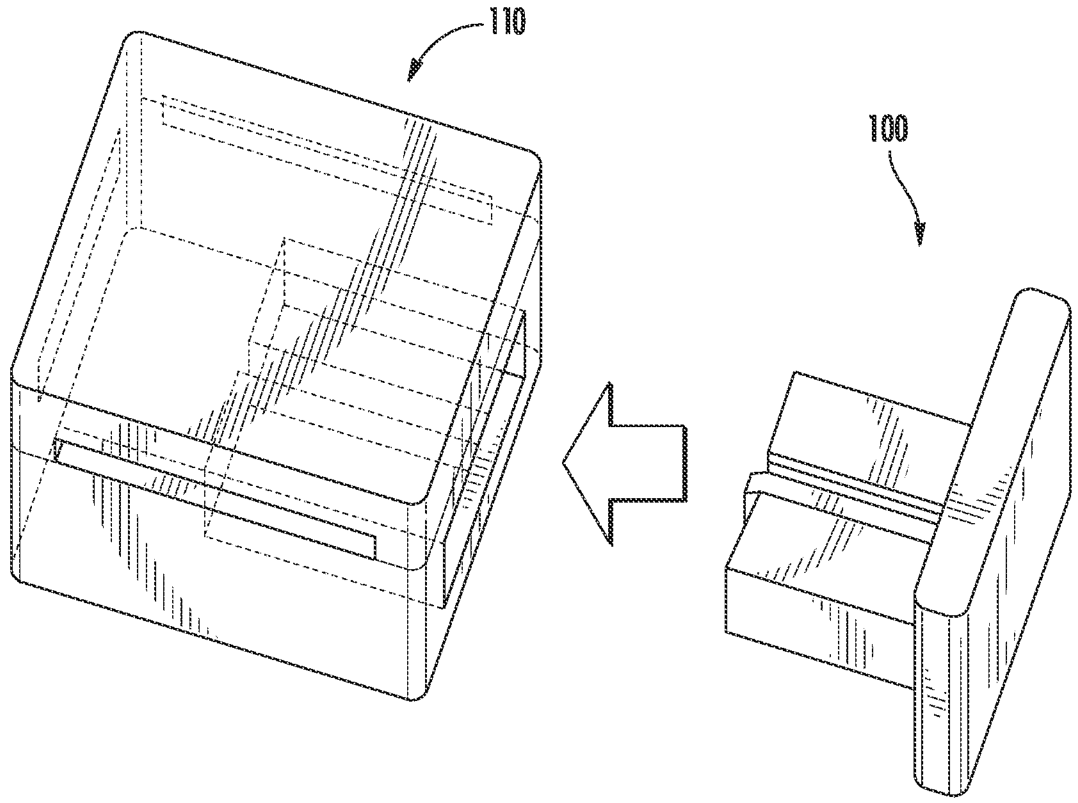
FIG. 1 provides a schematic drawing of a system including a cartridge and an assay reader according to one embodiment of the disclosure.

Reference numerals that are repeated across plural figures are intended to identify the same features in various implementations.

DETAILED DESCRIPTION

Any of the features, components, or details of any of the arrangements or embodiments disclosed in this application, including without limitation any of the cartridge embodiments and any of the testing or assay embodiments disclosed below, are interchangeably combinable with any other features, components, or details of any of the arrangements or embodiments disclosed herein to form new arrangements and embodiments.

Generally, the present disclosure is related to an assay device for determining a concentration of hemoglobin in a blood fluid sample. The assay device may be part of a POC testing system, for which exemplary embodiments are further discussed below. The device includes a separation membrane and a detection membrane located downstream from the separation membrane. The separation membrane is coated with a solution containing a cell lysing reagent, wherein the cell lysing reagent is present in the solution in an amount greater than 0.75 wt. % and less than 2.5 wt. % based on the wet weight of the solution. Additionally, the cell lysing reagent is present on the separation membrane in an amount greater than 200 micrograms/square centimeter to less than 675 micrograms/square centimeter based on the dry weight of the cell lysing reagent on the separation membrane after the solution has dried on the separation membrane. Further, the detection membrane is configured to elicit a quantifiable response in the presence of hemoglobin in the blood fluid sample. The quantifiable response corresponds to an amount of hemoglobin present in the blood fluid sample. In addition, the detection membrane is asymmetric and has a first plurality of pores located towards an upstream side of the detection membrane and a second plurality of pores located towards a downstream side of the detection membrane. The first plurality of pores have an average pore size that is larger than an average pore size of the second plurality of pores. The present disclosure also provides methods for using a vertical flow assay device to lyse the red blood cells in the blood fluid sample to quantify the level of the hemoglobin that is present in the blood fluid sample via reflectance spectroscopy from the downstream side of the detection membrane.

In particular, the assay device can be a vertical flow assay device that allows for the quantifiable response to be measured from the downstream side of the detection membrane, such as via reflectance spectroscopy, as opposed to the commonly used absorbance spectroscopy methods utilized by conventional assay devices for measuring the concentration of hemoglobin in a blood fluid sample, which allows for an electronics system that is easier to design. Further, reflectance spectroscopy does not require turbidity correction that is required in transmission spectroscopy, which can lead to erroneous results as discussed in detail above. In addition, because the blood fluid sample can be applied at the top of the device due to the vertical flow design, while the concentration of the target analyte is measured downstream at the bottom of the assay device (namely, at the detection membrane), the hemoglobin assay device can be easily included in a multi-analyte cartridge or multiplexed assay device. Further, while conventional devices commonly require the use of hazardous chemicals, the assay device of the present disclosure eliminates the need for such chemicals due to the specific features and arrangement of the separation membrane and the detection membrane.

With reference now to the figures, example embodiments of the present disclosure will be discussed in further detail. First, the components of the cartridge and assay reader will be discussed, followed by the components used to perform an assay as contemplated by the present disclosure.

FIG. 1 shows a point-of-care (POC) testing system according to one exemplary embodiment of the present disclosure. The POC testing system includes a cartridge 100 (comprising an embodiment of a proposed assay device) and an assay reader 110. As described herein, cartridge 100 is used to collect the blood fluid sample that may contain a target analyte such as hemoglobin, as well as any other target analytes of interest that the POC testing system is configured to measure. The collection process also distributes the blood fluid sample within cartridge 100. After the blood fluid sample is collected in cartridge 100, the user inserts cartridge 100 into assay reader 110. As described herein, the act of inserting cartridge 100 into assay reader 110 results in the compression of cartridge 100, thereby causing the blood fluid sample to be distributed to a separation membrane portion of an assay stack, the details of which are discussed in more detail below. In this way, the act of inserting cartridge 100 into assay reader 110 commences one or more assay reactions that provide information regarding the contents of the blood fluid sample. However, it is also to be understood that other insertion approaches are contemplated that do not require compression. Further, it is to be understood that while multiple assays can be utilized to determine the contents of a target analyte in the blood fluid sample, each assay is generally specific for one particular target analyte. As described herein, assay reader 110 is equipped with a detection system that is used to detect the results of the one or more assay reactions that occur at one or more membranes in an assay stack of cartridge 100. The detection system is not particularly limited and may be a detection system which causes a measurable signal change as the result of an assay reaction. Non-limiting examples of suitable detection systems include colorimetric, fluorescence, electrochemical, and optical detection systems as described herein and any other detection system that would be understood by one of ordinary skill in the art.

Figure 2A:
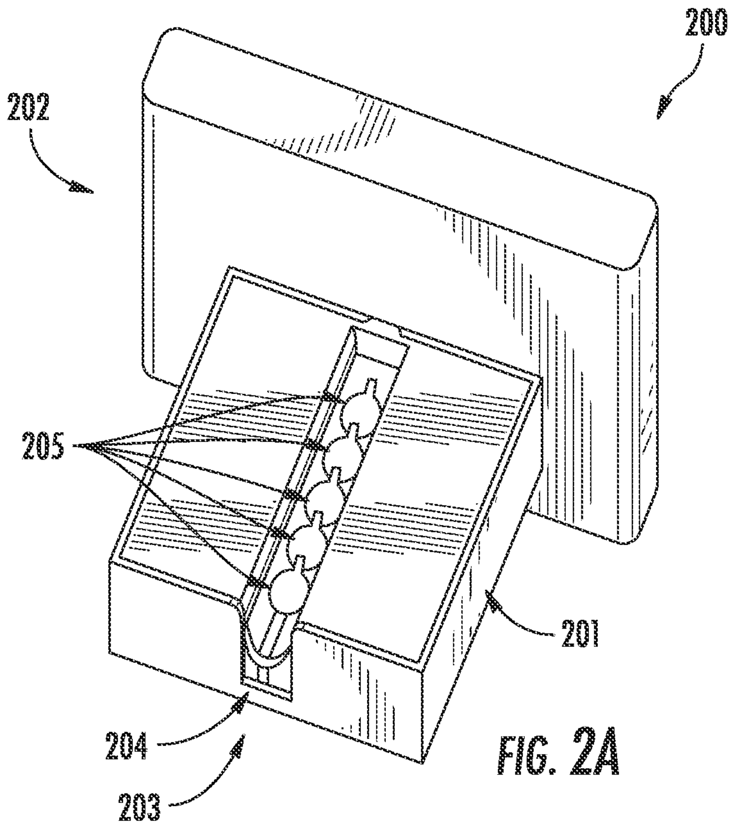
FIGS. 2A-2C illustrate an embodiment of the cartridge utilized in the system.
Figure 2B:
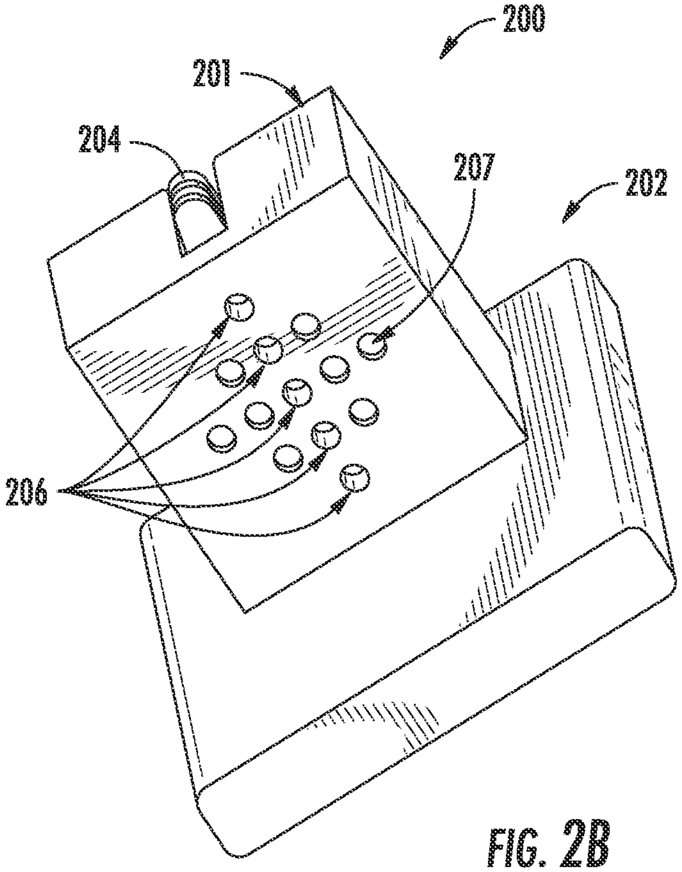

FIG. 2A illustrates a top, perspective view of an embodiment of cartridge 100 in the form of a cartridge 200. In FIG. 2A, cartridge 200 includes a housing 201 attached to a handle 202. In general, cartridge 200 is designed to be easy to handle by the user and to provide a protective shell for the microfluidic distribution system and assay components housed within cartridge 200, in general, suitable materials for housing 201 and handle 202 include polyolefinic compounds, such as polyethylene, polypropylene, and other polymeric resins or compounds known in the medical device manufacturing art. During sample collection, cartridge 200 is brought into contact with a fluid sample (e.g., the blood fluid sample). The fluid sample is drawn into channel 203 and via channel opening 204 by capillary action. In some embodiments, channel 203 includes a plurality of receiving chambers 205 located along channel 203. In some embodiments, each receiving chamber can be positioned between two venting holes, which facilitate the division of the fluid sample in the channel into multiple aliquots which flow to the assay stack. It should be recognized that the channel opening 204 can function as a venting hole and that neighboring receiving chambers can share a common venting hole between them. The venting holes can help to prevent unwanted bubble formation as the blood fluid sample is drawn into the receiving chambers. FIG. 2B illustrates a bottom view of an embodiment of the cartridge 200. In FIG. 213, the bottom portion of housing 201 includes a plurality of assay detection ports 206 aligned with channel opening 204. The assay detection ports 206 permit the assay results to be interrogated, for example, by optical detection methods as described herein. In addition, the bottom portion of housing 201 may include a plurality of holes 207, which are additional assay detection ports that may be used with assay components and microfluidic channels that are arranged in a corresponding configuration.

Figure 2C:
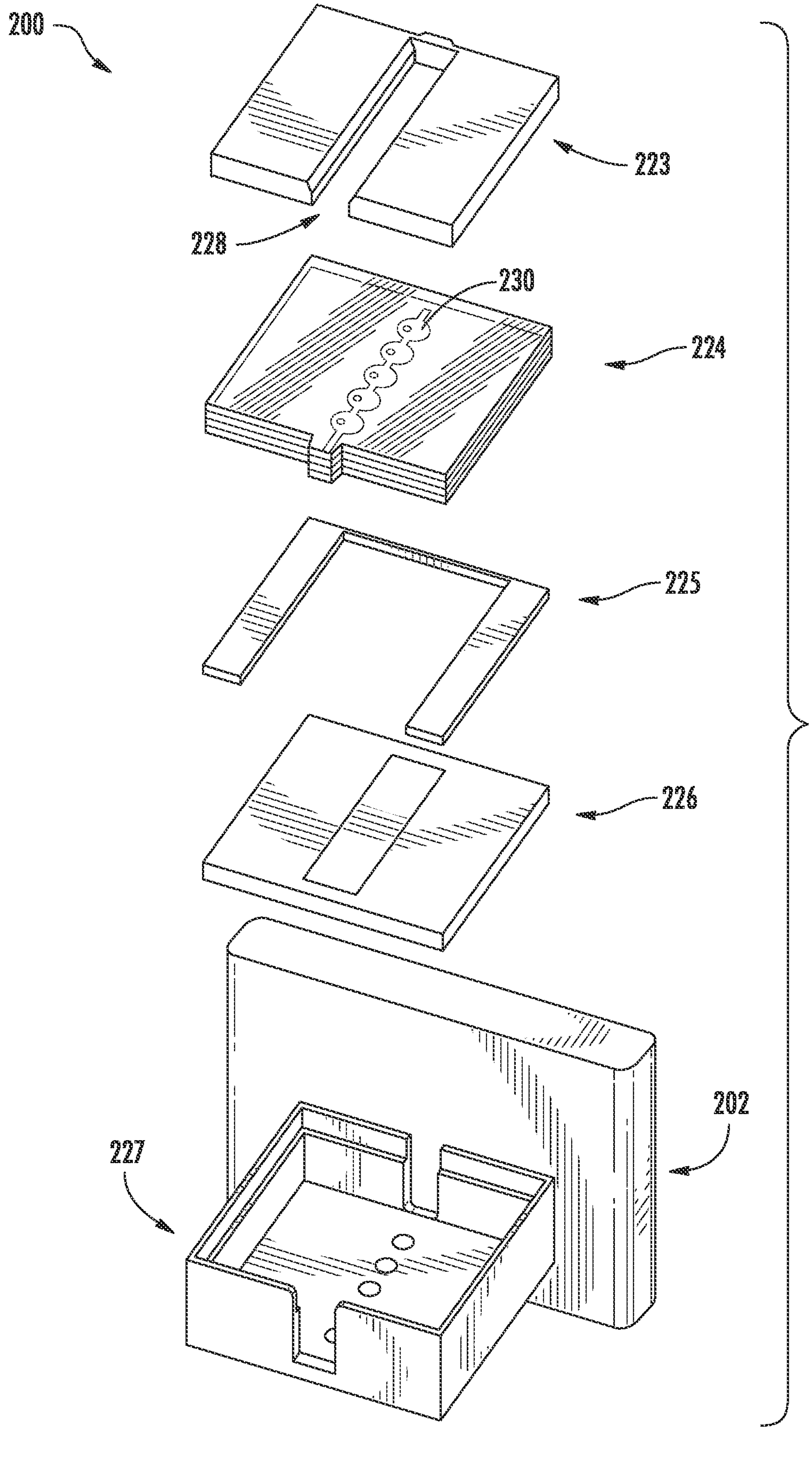

FIG. 2C provides an exploded view of the components of the cartridge 200, according to one embodiment of the present disclosure. In FIG. 2C, the outer shell of cartridge 200 includes the handle 202, bottom housing portion 227, and a cap 223 that is equipped with a slot 228. The bottom housing portion 227 can be a cuboid shape enclosure with one open side. The enclosure shape of the bottom housing portion 227 protects the components within the interior chamber and can avoid accidental actuation of the system. The cap 223 can fit to the open side of the bottom housing portion 227 and have a shape and size that corresponds to the open side of the bottom housing portion 227. When the bottom housing portion 227 and cap 223 of the housing are assembled together, an interior chamber can be formed for enclosing other components of the cartridge within the interior chamber. In other embodiments, the cap 223 and bottom housing portion 227 do not form an enclosure with an interior chamber and can be rigid structures positioned on the top of a metering stack and bottom of an assay stack, which are described herein.

In preferred embodiments, bottom housing portion 227 and cap 223 can be formed of a material to provide a rigid structure to the cartridge 200. For example, the bottom housing portion 227 and the cap 223 can be a plastic material, as described herein. The bottom housing portion 227 and cap 223 can be moveable or non-moveable with relation to each other. In some embodiments, when cartridge 200 is inserted into an assay reader, the components within the interior chamber are compressed to cause at least one portion of the collected blood fluid sample to be delivered to a plurality of assay components. The compression can be caused by the user closing a lid of the assay reader, for example. However, it is also to be understood that other approaches for insertion of the cartridge 200 into an assay reader are contemplated that do not require compression.

In some embodiments, the cartridge does not include a cap and bottom housing portion. In such embodiments, the cartridge does not include the housing 201 (see e.g., FIG. 2A) and the metering stack and assay stack can be inserted into an assay reader without an enclosure around it.

As shown in FIG. 2C, cartridge 200 can include a metering stack 224, a spacer material 225, and an assay stack 226. The metering stack 224 can be used to collect a sample of a biological fluid (e.g., a blood fluid sample) and the assay stack 226 can include assay components necessary for a target analyte (e.g., hemoglobin) concentration assay to be carried out through one or more of the receiving chambers 205 as discussed in detail herein. However, it should also be understood that other assays (e.g., immunoassays or enzymatic assays) may also be carried out in additional receiving chambers 205 and the assay stacks 226 associated with each receiving chamber 205 can each be unique based on the particular assay associated with each receiving chamber 205. As used herein, the term "metering" refers to collecting a liquid sample of a biological fluid and delivering one or more predetermined volumes of at least a portion of the fluid to the assay components for further analysis via the assay components contained in the assay stack. When assembled into a cartridge, the metering stack 224, a spacer material 225, and an assay stack 226 can be arranged in a stack.

The spacer material 225 is a compressible layer that may be positioned between the metering stack 224 and assay stack 226 as shown in FIG. 2C. In an embodiment, the spacer material 225 may be a flexible material that can be compressed in the vertical direction when the cartridge is inserted into the assay reader and the metering stack 224 is moved into contact with or close proximity to the assay stack 226. In some embodiments, the spacer material 225 can be a flexible material, such as foam, rubber, porous polymer, metal, cotton, or other bending, folding, or moving mechanisms such as a clamp or spring. In some embodiments, the metering and assay stacks are initially separated by an air gap maintained by the spacer material 225. In certain embodiments, spacer material 225 is physically affixed to another layer, such as metering stack 224 or assay stack 226 before the layers of the cartridge are brought together. Typically, the metering and assay stacks remain separated throughout the sample collection process. In such embodiments, the separation between the metering stack and the assay stack can prevent a chemical reaction from starting during the blood fluid sample collection step. When the spacer material 225 is compressed, the metering stack 224 and assay stack 226 can come into contact with or brought into close proximity to each other.

In preferred embodiments, when the metering stack is fully filled with a biological fluid, the cartridge is inserted into an assay reader. Preferably, the material that is used for the top surface of channel 230 is sufficiently transparent so that a user can determine by visual inspection when the channel 230 is filled and the cartridge is ready for insertion into the assay reader. The assay reader is configured to accept the cartridge and includes a mechanism that compresses the spacer material, thereby pushing the metering stack and assay stack together when the cartridge is inserted into the assay reader. The compression of the spacer material causes a predetermined volume of at least a portion of the collected fluid to flow to assay components in the assay stack. In this way, the act of compressing the metering stack and assay stack together can, in certain embodiments, provide a well-defined point in time that marks the start of the assay through the components in the assay stack. However, it is also to be understood that other insertion approaches are contemplated that do not require compression of the metering stack and assay stack together as would be understood by one of ordinary skill in the art.

In some embodiments, the fluid sample containing the target analyte is blood, and the cartridge can be used to collect a sample of blood from a skin prick and deliver the sample to the assay stack consistently with minimal user intervention. The user, with a regular pricking lancet, can elicit bleeding in a suitable body site such as a fingertip, palm, hand, forearm, stomach area, etc. Once a drop of blood of sufficient volume is on the skin, the user can collect it by touching the tip of the cartridge to the blood drop. Once the metering stack is fully filled with blood, the user can insert the cartridge into the assay reader, which triggers the delivery of the blood sample to the assay stack. In some embodiments, this can be performed by a patient, administrator, or healthcare provider. The blood collection and testing as described herein does not have to be performed by a trained heath care professional.

In addition, the cartridge design can allow for dispensing different pre-defined volumes of blood sample to multiple assay locations, without using any moving parts such as pumps or valves in the cartridge or in the assay reader. This increases the accuracy and flexibility of a multiplexed quantitative POC analysis, while reducing the complexity and cost of the cartridge and the assay reader.

Typically, as illustrated in FIG. 2C, the metering stack 224 includes a channel 230 to contain the biological fluid (e.g., a blood fluid sample containing a target analyte). In certain embodiments, the channel 230 can hold a volume of biological fluid containing a target analyte in the range of about 0.5 μl to about 100 μl, about 5 μl to about 90 μl, about 10 to about 80 μl, about 20 μl to about 60 μl, or about 30 μl to about 50 μl. The volume of the biological fluid can be controlled by the dimensions of the channel, including the shape, width, length, and depth of the channel, as described herein. In some embodiments, the depth of the channel can be in the range of about 5 μm to about 3 mm, about 10 μm to about 2 mm, or about 250 μm to about 1 mm. In some embodiments, the width of the channel can be in the range of about 100 μm to about 10 mm, about 250 μm to about 5 mm, about 500 μm to about 3 mm, or about 750 μm to about 1 mm. In certain preferred embodiments, the dimensions of the channel are selected such that the biological fluid is drawn into the channel by capillary action.

Preferably, the metering stack 224 is designed to direct the biological fluid to flow into the channel 230 and into any receiving chamber(s) that may be present. In some embodiments, the channel 230 can be formed of or coated with a hydrophilic material, non-limiting examples of which include 93210 hydrophilic PET (Adhesives Research, Glen Rock PA) or 9984 Diagnostic Microfluidic Surfactant Free Fluid Transport Film. 9960 Diagnostic Microfluidic Hydrophilic Film, or 9962 Diagnostic Microfluidic Hydrophilic Film (3M Oakdale, MN). The channel 230 can also have one or more porous or mesh material(s) along some portions of the channel 230 that allows at least a portion of the biological fluid containing the target analyte to be dispensed from the channel 230 of the metering stack 224 to contact assay components in the assay stack. In one non-limiting embodiment, the metering stack layer includes a porous or mesh material that can be positioned such that the porous or mesh material is aligned with the part of the channel portion on the metering stack's top surface and part of the assay distribution ports and assay components on the metering stack's bottom surface. In some embodiments, the porous or mesh material is selected such that the pores in such material separate the target analyte into a portion that is to be delivered to the assay components and a portion that is not delivered to the assay components. In this way, when the cartridge is inserted into the assay reader to perform the assays, only plasma is delivered to some of the assay components for analysis. Of course, combinations of porous or mesh materials may be used such that the entire biological fluid is delivered to some of the assay components, while only portions of the biological fluid may be delivered to other assay components. For example, the combination of porous or mesh materials may allow only plasma to reach some assay components but allow for the delivery of all blood components to other assay components, such as when it is desirable to measure hemoglobin concentration, which requires the lysing of red blood cells in a downstream layer of the device past the metering stack.

In certain embodiments, the channel can include a porous or mesh material at the bottom of the channel. Further, the porous or mesh material at the bottom of the channel can be a hydrophilic material or a material coated with a hydrophilic coating or treatment. In some embodiments, the porous or mesh material can have a pore size between about 1 μm to about 500 μm. Advantageously, when the biological fluid containing the target analyte is blood, the pores of the porous or mesh material can be sized to allow the porous or mesh material to hold the blood sample in the channel without dripping during blood collection and to be absorbed by the assay stack during the blood dispensing step which occurs upon insertion of the cartridge into the assay reader. In some embodiments, the porous or mesh material can also be used to release air and prevent bubble formation during the time that channel is filled with the biological fluid.

Figure 3:
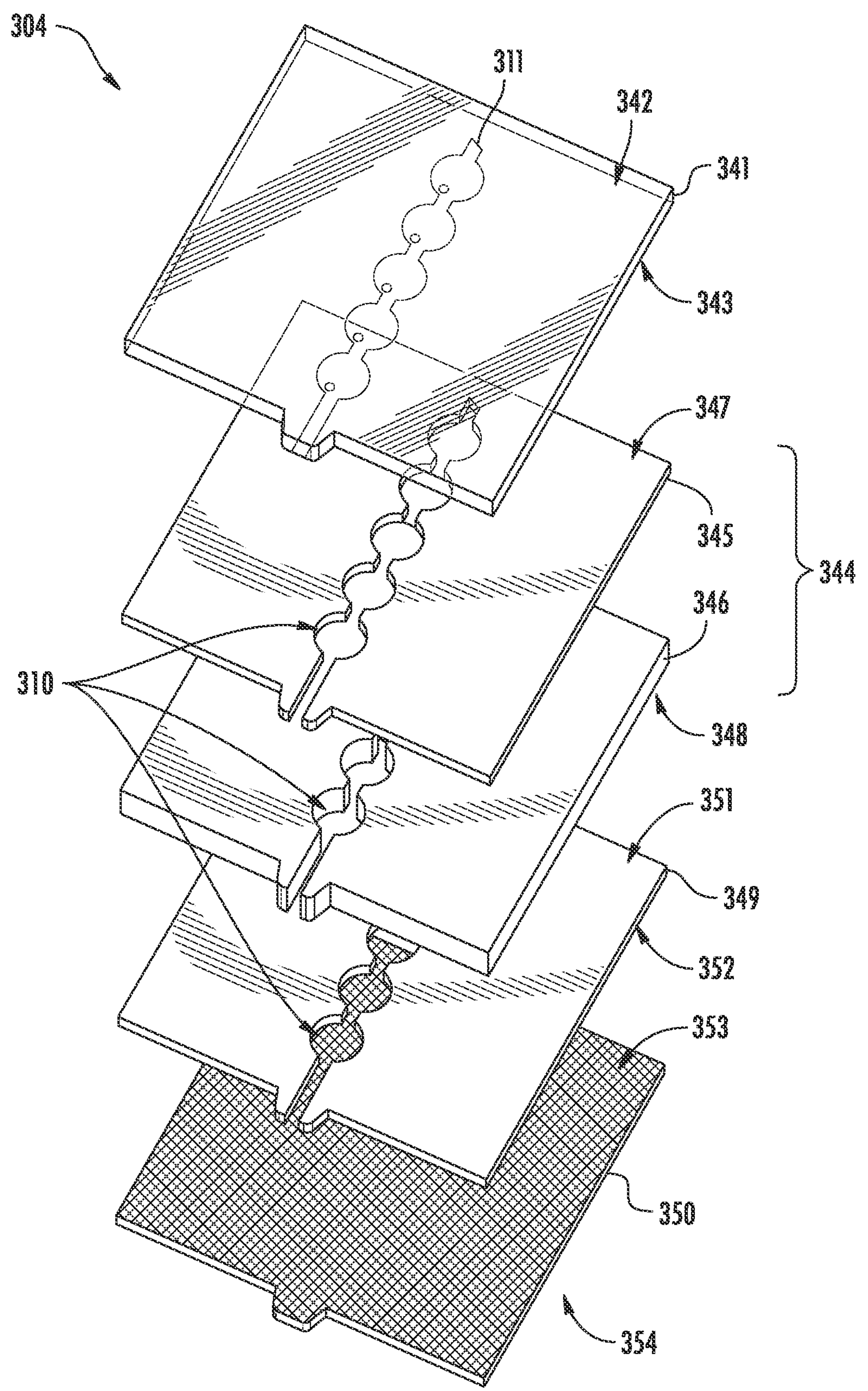
FIG. 3 illustrates various layers of a metering stack contained within the cartridge.

FIG. 3 illustrates an exploded view of a metering stack 304 according to one exemplary embodiment of the present disclosure, where such metering stack 304 can be used as metering stack 224 in the embodiment of FIGS. 2A to 2C. In FIG. 3, the metering stack 304 is formed by assembling multiple layers. The first layer 341 can be a plastic sheet with a first side 342, which is in communication with the surrounding environment when the cartridge is located outside the assay reader, and a second side 343 that faces the assay stack. In some embodiments, the first layer 341 may be a cover layer or top layer of the metering stack. In preferred embodiments, first layer 341 may have a hydrophilic surface or coating on second side 343, Non-limiting examples of suitable hydrophilic surfaces coatings include polyvinylpyrrolidone-polyurethane interpolymer, poly(meth)acrylamide, maleic anhydride polymers, cellulosic polymers, polyethylene oxide polymers, and water-soluble nylons or derivatives thereof, to name just a few. The presence of the hydrophilic surface or coating on second side 343 helps to draw the biological fluid (e.g., blood fluid sample) into the channel. The first layer 341 may include venting holes 311 positioned to align with the channel 310 defined by the layers below. In FIG. 3, for example, the venting holes 311 are aligned with the receiving chambers of channel 310 to allow air that otherwise would be trapped as an air bubble in the receiving chamber during channel filling to escape efficiently into the surrounding environment. It should be noted that the channel opening can also serve as a vent hole, if desired. In certain preferred embodiments, the first layer 341 includes polyethylene terephthalate (PET) with a hydrophilic coating on the second side 343 and venting holes 311.

The second layer 344 is positioned below the first layer 341 on the second side or assay facing side of the first layer 341. The second layer 344 itself can be a combination of one or more layers as illustrated in FIG. 3. Regardless of whether the second layer includes one layer or more than one layer, the second layer essentially defines the shape and size of channel in the metering stack, including any receiving chambers that may be part of the channel. For example, the second layer 344 can be formed from one or more layers of polymeric material cut to define the volume and shape of the channel 310 that can contain the biological fluid blood fluid sample). Other non-limiting methods of forming the channel 310 include injection-molding, stamping, machining, casting, laminating, and 3-D printing. Combinations of such fabrication techniques are also expressly contemplated by the present disclosure. In the embodiment shown in FIG. 3, second layer 344 has a first side 347 facing the first layer 341 and an opposite, second side 348 that faces the assay stack. Furthermore, second layer 344 includes adhesive layer 345 and plastic layer 346. Adhesive layer 345 fastens the first layer 341 to plastic layer 346. In some embodiments, the second layer 344 can be a combination of one or more plastic layer(s) 346 and adhesive layers 345. Preferably, adhesive layer 345 or plastic layer 346 or both are fabricated from materials which present a hydrophilic surface to the interior surfaces of the channel 310 in order to facilitate the distribution of the biological fluid within channel 310. In some embodiments, the hydrophilic plastic sheet(s) can include a PET material with a channel 310 cut into it. If desired, channel 310 may include one or more receiving chambers as shown in FIG. 3. Thus, the thickness and geometry of channel 310 can control the volume of sample to be collected. The hydrophilic interior surfaces of the channel 310 allow the metering stack to collect blood sample by capillary force. In some embodiments, the first layer 341 and the second layer 344 can be one integrated layer used in the metering stack 304.

In FIG. 3, third layer 349 can be formed from a hydrophobic adhesive layer. Non-limiting examples of suitable materials for fabricating third layer 349 include 3M 200MP adhesive or 3M 300MP adhesive (3M, Oakdale, MN). In preferred embodiments, the same channel geometry as channel 310 is cut into the third layer to match channel 310 cut in the second layer. In some embodiments, the third layer 349 can have a first side 351 facing the second layer 344 and a second side 352. In some embodiments, the third layer 349 can define the hydrophilic region in a fourth layer 350 positioned below or on the second side 352 of the third layer.

In some embodiments, the fourth layer 350, which can be positioned beneath only a portion of the receiving chambers of the channel 310, can be a hydrophilic mesh or porous material. In some embodiments, substantially all of the fourth layer 350 can include the mesh or porous material as shown in FIG. 3. In other embodiments, the hydrophilic mesh or porous material can be a portion of the fourth layer 350. In some embodiments, such as the example shown in FIG. 3, the fourth layer 350 can have a first side 353 facing the third layer 349 and an opposite assay stack-facing second side 354. The hydrophobic third layer 349 can be positioned above the fourth layer 350. The hydrophobic third layer 349 can be a hydrophobic adhesive layer to define a wettable region of the mesh or porous material of the fourth layer 350.

The method used to fabricate the metering stack is not particularly limited, so long as it is compatible with the general manufacturing requirements for medical devices, in certain embodiments, the layers that constitute the metering stack are first fastened together as large multilayer sheet or strip which is then subjected to stamping or cutting processes to form the metering stack, including the channel and any receiving chambers that may be present. In some embodiments, the first layer 341 and second layer 344 can be combined in one piece of plastic material with a hydrophilic surface forming the channel. Various other combinations of two or more layers, as well as additional layers, are contemplated by various embodiments.

In the POC systems of the present disclosure, the assay reactions occur in the assay stack. In general, an assay stack includes one or more "assay components." As used herein, the term "assay component" refers to one or more of the active component and a passive supporting element or mask, including but not limited to the multiplexed assay pads. The number of assay pads (e.g., separation membranes, detection membranes, etc.) in a particular assay component is not particularly limited but is based on the particular assay requirements needed to diagnose the condition or analyze the fluid sample of the patients for whom the assay stack is designed. In preferred embodiments, the layers of the assay pads of a given assay component align vertically with the appropriate regions of the channel in the metering stack above to ensure that a predetermined volume of a biological fluid, sufficient to perform the assay associated with the particular target analyte of interest, is delivered to the detection membrane. The assay pads can act as a wick that draws the sample through the metering stack into the assay stack, for example through capillary action, gravity, etc. Therefore, once the metering stack and the assay stack are in contact with or within close proximity to each other, the biological fluid to be analyzed is directed to move into the detection membrane, where it may encounter one or more reagents required to perform the assay associated with the particular assay component. If desired, the assay stack may include additional layers that contain reagents required for the completion of the assay. The number of layers required can depend on the number of chemical reactions that need to take place in order to complete the assay. In various embodiments, layers of the assay stack can be made of variously shaped and variously-sized pads of different porous membrane materials, non-limiting examples of which include a polysulfone, a polyethersulfone, nylon, cellulose (e.g., nitrocellulose, cellulose filter paper, etc.) and glass fiber.

The type of assays that may be performed using the assay systems of the present disclosure are not particularly limited and can be any assay for which the required reagents can be stably incorporated into one or more separation membranes and/or detection membranes and which can cause a change that can be detected by the assay reader. In some embodiments, the assay reactions cause a color change, which may be detected using the colorimetric detection methods as described herein. Still other assay reactions may result in another optical change, a fluorescence change, an electrochemical change, or any other detectable change that may occur in a detection membrane of the assay stack. In certain embodiments, the assays may be porous material-based lateral flow assays, vertical flow assays, and/or a combination of lateral and vertical flow assays. In general, the target analyte is contained within a biological fluid, non-limiting examples of which include blood, plasma, serum, saliva, sweat, urine, lymph, tears, synovial fluid, breast milk, and bile, or a component thereof, to name just a few. In certain preferred embodiments, the biological fluid is blood. For example, in one embodiment, the assay systems of the present disclosure are useful for providing patients with POC information regarding target analytes in their blood composition. In particular, the assay systems of the present disclosure can be used to determine the concentration of hemoglobin and optionally other analytes in a blood fluid sample. Other analytes that can be measured in blood via other receiving chambers that may be present as part of the assay system include thyroid markers (e.g., T3, free T4, thyroid stimulating hormone, etc.), inflammatory markers (e.g., C-reactive protein, etc.), vitamins (detected via a competitive assay structure), cholesterol, lipoproteins, triglycerides, metabolic syndrome markers, glucose, glycated albumin, and serological levels of antibodies against a disease (detected by a labeled antigen architecture).

Figure 4:
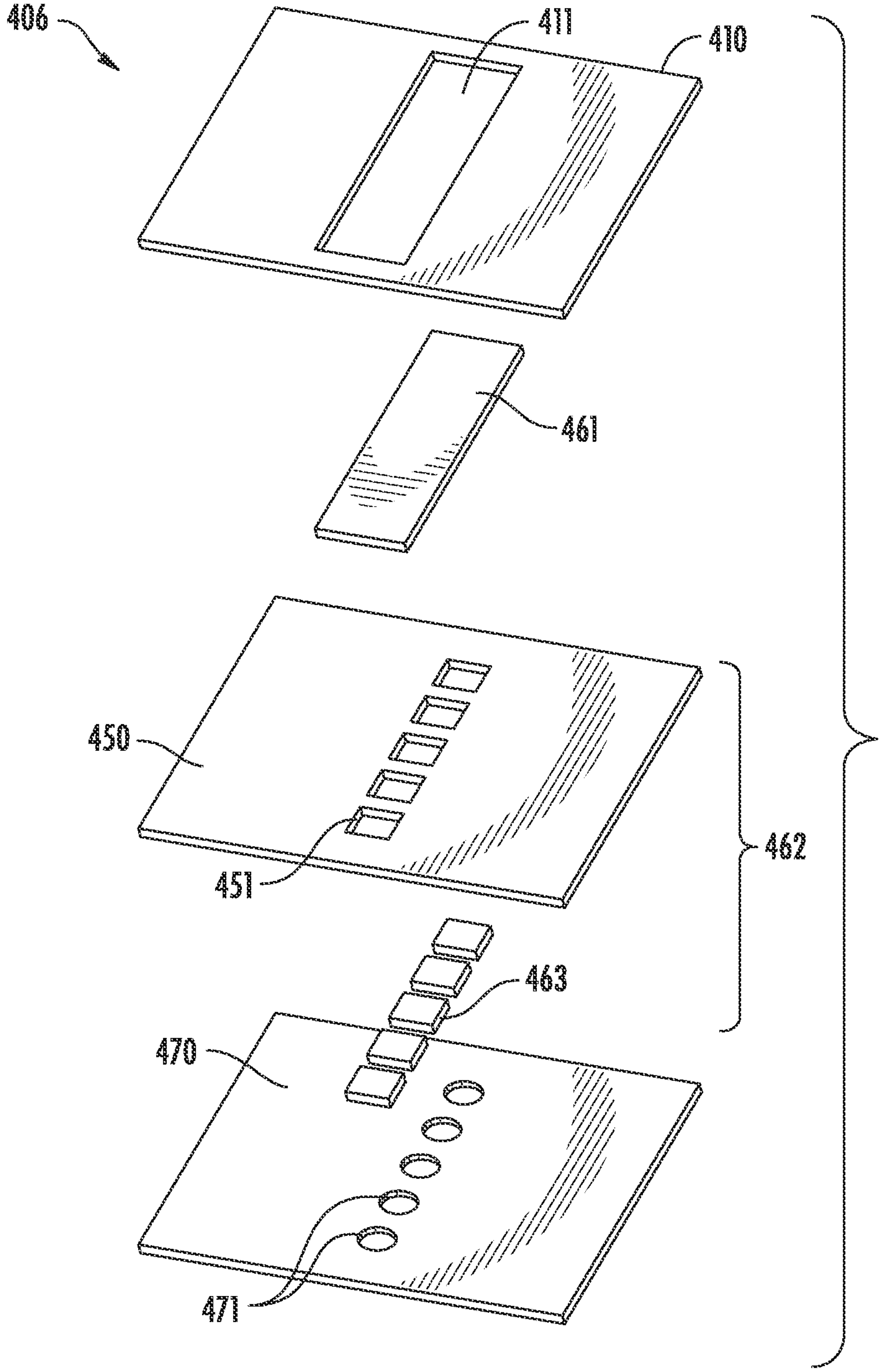
FIG. 4 illustrates various layers of an assay stack contained within the cartridge.

FIG. 4 illustrates an exemplary assay stack 406 according to one embodiment of the present disclosure, where such assay stack 406 can in particular be used as assay stack 226 in the embodiment of FIGS. 2A to 2C. In FIG. 4, the assay stack 406 is formed of multiple layers, including one or more of the layers with active components and a passive supporting element or mask. More specifically, in FIG. 4, assay stack 406 includes assay stack cover layer 410 that features a cut-out portion 411 that is aligned with the channel in the overlying metering stack. Generally, assay stack cover layer 410 is fabricated from a polymeric material that provides rigidity to the assay stack and provides ease of handling during manufacturing of the cartridge. Furthermore, the cut-out portion 411 allows the biological fluid to flow past the assay stack cover layer 410 towards the underlying assay components when the cartridge is inserted into the assay reader, as described herein. As shown, the assay stack 406 includes a separation membrane 461 which can be the top-most layer facing the metering stack. The separation membrane 461 is used to separate components of the biological fluid (e.g., blood fluid sample) to prevent undesirable components from reaching the underlying assay components. For example, when the biological fluid is a blood fluid sample and the assay is focused on determining the concentration of hemoglobin in the blood fluid sample, the separation membrane 461 is designed specifically to burst the red blood cells to release hemoglobin so that the hemoglobin can pass through to the detection membrane portion of the assay stack 406 after the cartridge has been inserted into the assay reader. Further, it should be understood that the lysed red blood cells that pass through to the detection membrane do not interfere with the determination of the concentration of the hemoglobin the detection membrane. Such a separation membrane 461 can be made of a variety of materials, non-limiting examples of Which include sulfone polymers, mixed cellulose esters, or a combination thereof as discussed in more detail below. In some embodiments, the fabrication of the separation membrane can include surface treatments for improved wettability and/or other properties. The plasma separation membrane can be one continuous piece of membrane for all of the assay components, or multiple discontinuous pieces of membrane material that may be the same or different (or some combination thereof) for each of the detection membranes in the assay component in the assay stack FIG. 4. When the separation membrane 461 is discontinuous, cross-talk between neighboring assays can be prevented. In some embodiments, some of the detection membranes of an assay component have a corresponding separation membrane, while other detection membranes do not have such a layer. Other additional components and features of the separation membranes of the assay devices contemplated by the present disclosure are discussed in more detail with respect to FIGS. 8A-8D.

As shown in FIG. 4, in some embodiments, the assay stack 406 can include an assay component 462 positioned below the separation membrane 461. The assay component 462 includes a mask support layer 450 with a plurality of cut-outs 451 that are configured to receive and immobilize detection membranes 463 when the assay stack 406 is assembled. Preferably, cut-outs 451 are positioned to align detection membranes 463 with separation membranes 461 such that the biological fluid containing the target analyte will flow from separation membranes 461 into detection membranes 463. Detection membranes 463 (e.g., detection membranes such as but not limited to color generation membranes) may include reagents that are necessary to complete the assay reactions that are initiated once the target analyte (e.g., hemoglobin) flows through the separation membranes 461. In some embodiments, detection membranes 463 serve as a detection indicator layer that provides information corresponding to the results of the assay performed. For example, detection membranes 463 (e.g., color generation membranes) can include a visual indicator, such as a color change, to indicate the results of the assays, although it is to be understood that the detection membranes contemplated by the present disclosure also contemplate fluorescent and electrochemical changes or responses. Furthermore, while assay stack 406 in FIG. 4 contains only assay component 462, it should be understood that the assay stack 406 may contain additional assay components with assay pads that are impregnated with the reagents required to complete and/or report the results of a particular assay. For instance, the assay stack 406 can include any number of assay components necessary to perform the analysis of the blood sample. Because some assays require more chemical steps than others, assay components may include more non-functional assay pads which only serve to draw the completed assay products to the bottom of the assay stack, where the results may be detected by the assay reader, as described herein.

Assay stack 406 in FIG. 4 also includes an assay bottom layer 470, which is typically fabricated from a polymeric material to provide mechanical strength and ease of handling of assay stack 406 during the manufacturing process. In addition, assay bottom layer 470 typically includes a plurality of detection ports 471 which are aligned with the detection membranes of the assay stack and sized to permit interrogation of the assay results by the assay reader.

Figure 5A:
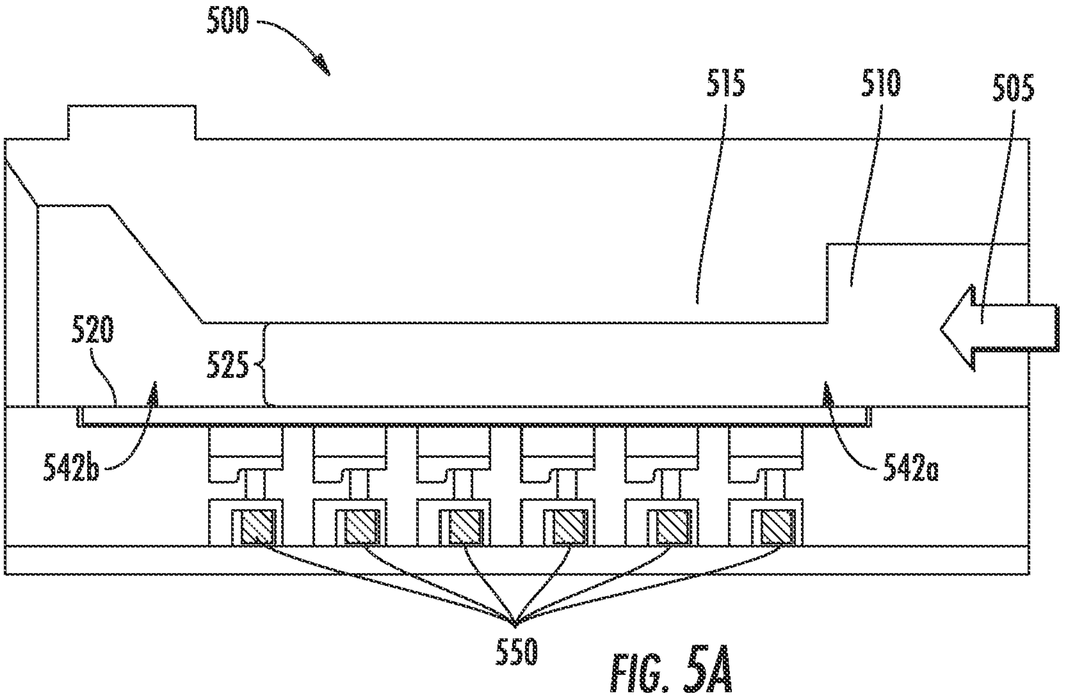
FIG. 5A shows a longitudinal cross sectional view of an assay reader according to one embodiment of the disclosure.

FIG. 5A shows a schematic drawing of an assay reader, in longitudinal cross-section, according to one non-limiting embodiment of the present disclosure. In FIG. 5A, assay reader 500 includes cartridge receiving chamber 510 which houses the cartridge when it is inserted as indicated by arrow 505. Tab 515 runs longitudinally along assay reader 500 and extends into cartridge receiving chamber 510. Tab 515 is configured to insert into a slot at the top of the cartridge, such as slot 228 in FIG. 2C, when the cartridge is inserted into the assay reader. In addition, the spacing 525 between the bottom edge of tab 515 and support surface 520 is set such that when the cartridge is inserted, tab 515 compresses the metering stack and the assay stack together, thereby causing the biological fluid containing the target analyte to flow from the metering stack into the assay stack and initiating the assay reactions. In certain embodiments, the assay reader may include a snap-fit mechanism that locks the cartridge in place once it has been fully inserted into the assay reader. This is advantageous because it prevents the user from accidentally removing the cartridge from the assay reader before the assays are complete, which could adversely affect the accuracy of the assay results. In some embodiments, assay reader 500 also includes sensors 542*a* and 542*b*, which detect and time the insertion of the cartridge. For example, as the cartridge is inserted into cartridge receiving chamber 510 and begins to engage with tab 515, the bottom surface of the cartridge may pass over sensor 542*a*, which is detected by appropriate electronics as the beginning of the insertion of the cartridge. The second sensor 542*b* is located further inside the assay reader 500 and detects the presence of the cartridge when the cartridge is fully inserted as well as the time at which full insertion occurred. Assay reader 500 may then compare the overall time for insertion of the cartridge to determine if the insertion of the cartridge was timely and proper. In this way, the assay reader will not perform any assay readings in situations where (1) the cartridge was only partially inserted, or (2) the cartridge was partially inserted, removed, and inserted again. Either case could give inaccurate assay readings, due to the incomplete compression of the metering stack and assay stack, resulting in incomplete delivery of the required amount of target analyte to the detection membranes in the assay stack.

Figure 5B:
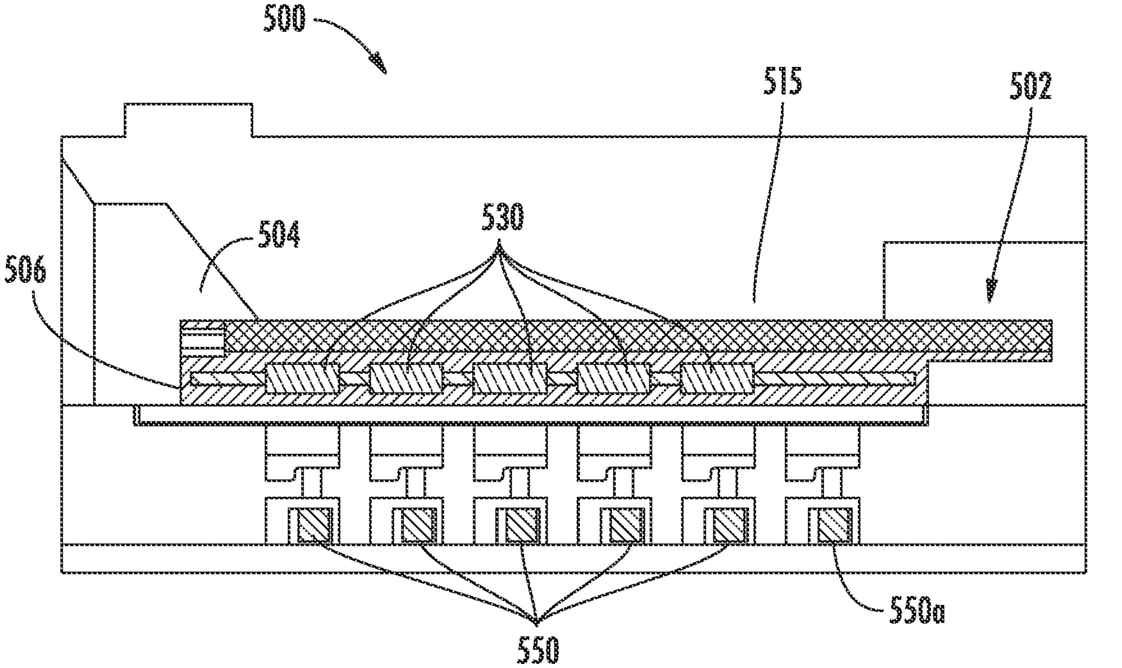
FIG. 5B shows a longitudinal cross sectional view of an assay reader with an inserted cartridge according to one embodiment of the disclosure.

In the exemplary embodiment shown in FIG. 5A, assay reader 500 detects the results of the assay by detecting the color change of the detection membrane caused by the assay reactions. To achieve this, assay reader 500 includes a plurality of light sources (not shown in this cross-sectional drawing) and light detection elements 550 arrayed within assay reader 500 such that they align with the detection membranes located in the downstream direction of the cartridge compared to where the biological fluid sample is applied at an upstream location when the cartridge is fully inserted. In order for light detection elements 550 to be able to detect the color of the detection membranes, support surface 520 may be equipped with one or more apertures or be fabricated from a transparent material that allows light to penetrate therethrough. However, it is also to be understood that the assay reader 500 can alternatively include components to detect electrochemical or fluorescent changes in a detection membrane portion of the assay stack. FIG. 5B shows a schematic illustration of a longitudinal cross-section of assay reader 500 with cartridge 502 fully inserted. Cartridge 502, which may correspond to cartridge 100 or 200 of FIG. 1 or FIGS. 2A to 2C, includes metering stack 504 and assay stack 506, which are compressed together by tab 515 such that the target analyte (e.g., hemoglobin) is delivered from the metering stack 504 to the detection membranes 530. Detection membranes 530 are aligned with light detection elements 550. Note, however, that assay reader 500 may include an additional light detection element 550*a* without a corresponding detection membrane 530. The presence of additional light detection elements, such as light detection element 550*a*, allow the assay reader to be used with different types of cartridges for different assays, particularly cartridges that may be designed to perform more assays, as well as to identify the different types of cartridges for the different assays.

In particular, it is to be understood that the assay reader 500 of FIGS. 5A-5B can be utilized in reflectance spectroscopy to determine the concentration of the target analyte (e.g., hemoglobin) in a blood fluid sample that has been introduced upstream of the detection membrane, while the analysis is taken downstream where the detection membrane is located in the cartridge 502 since the device is a vertical flow assay device. As known by one of skill in the art, reflectance spectroscopy refers to measuring light as a function of wavelength that has been reflected or scattered from a surface, in this case the detection membrane. The use of reflectance spectroscopy lends itself well to POC diagnostics as it allows for dry chemistry techniques to be used in the manufacturing process, simplified design of the electronics, and the advantage of using a vertical flow architecture for sample collection and delivery. Further, reflectance spectroscopy does not require turbidity correction that is required in transmission spectroscopy, which can lead to erroneous results as discussed in detail above.

Figure 6A:
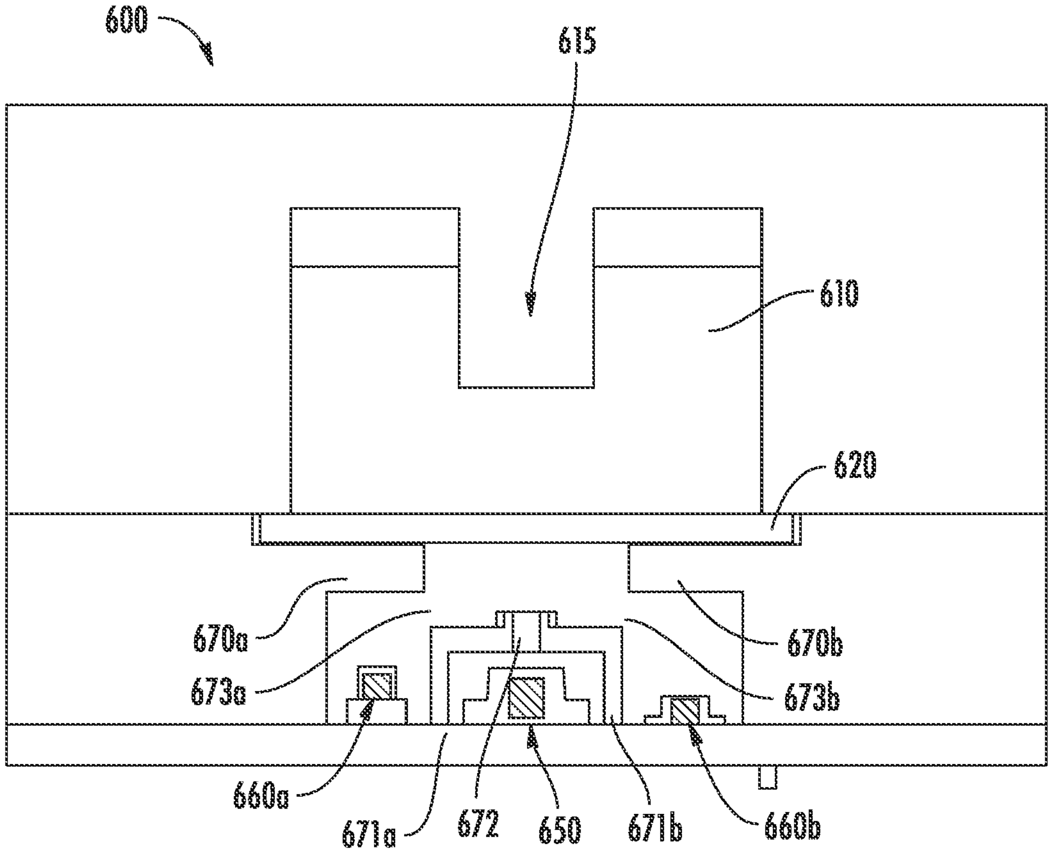
FIG. 6A shows a transverse cross-sectional view of an assay reader according to one embodiment of the disclosure.

FIG. 6A shows a schematic drawing of a transverse cross-section of the assay reader shown in FIGS. 5A-5B in the form of an assay reader 600 that may be used to detect color changes. In FIG. 6A, the assay reader 600 includes a tab 615 that extends into cartridge receiving chamber 610 to engage with a slot on the cartridge. Such engagement then compresses the metering stack and the assay stack against support surface 620, initiating the assay reactions. Light sources 660*a* and 660*h* provide light for detecting the assay results and are positioned near light detection device 650. Specifically, as illustrated in FIG. 6A, light sources 660*a* and 660*b* provide light to analyze the detection membrane via reflectance spectroscopy corresponding to light detection device 650. In general, it is advantageous to dedicate one or more light sources to each light detection element in order to ensure that the photon flux onto the light detection element is sufficient to obtain an accurate reading. In some embodiments, the light sources dedicated to a particular light detection element have the same output spectrum. In other embodiments, however, the light sources corresponding to a given light detection element produce different output spectra. For instance, the light sources may be light emitting diodes (LEDs) that produce different colors of light. In general, it is advantageous to include optical elements to direct the light and/or reduce the amount of light scattering in the assay reader. In some embodiments, the optical elements are apertures that only allow light emanating from the light source that is line-of-sight to the respective detection membrane to reach the detection membrane. For example, in FIG. 6A, light source 660*a* is limited by aperture defining members 670*a* and 671*a* such that only the light from light source 660*a* that passes through aperture 673*a* will reach the detection membrane and subsequently be detected by light detection device 650. Similarly, light source 660*b* is limited by aperture defining members 670*b* and 671*b*, such that only the light from light source 660*b* that passes through aperture 673*b* will reach the detection membrane and subsequently be detected by light detection device 650. In preferred embodiments, aperture defining members 670*a*, 670*b*, 671*a*, and 671*b* are fabricated from a black matte material to reduce the amount of undesirable scattering when light sources 660*a* and 660*b* are turned on. Furthermore, in this embodiment, light detection device 650 located in a housing includes aperture defining members 671*a* and 671*b* that only permit light that passes through aperture 672 to reach light detection device 650. If desired, the aperture 672 may be fitted with a filter to admit only light of a predetermined wavelength or wavelength range for detection by light detection device 650. This may be useful, for example, when the light sources are equipped to provide only white light for colorimetric analysis. In addition, the light from light sources 660*a* and 660*b* and the light to be detected by light detection device 650 may be directed or manipulated using optical elements such as lenses, filters, shutters, fiber optics, light guides, and the like without departing from the spirit and the scope of the present disclosure.

Figure 6B:
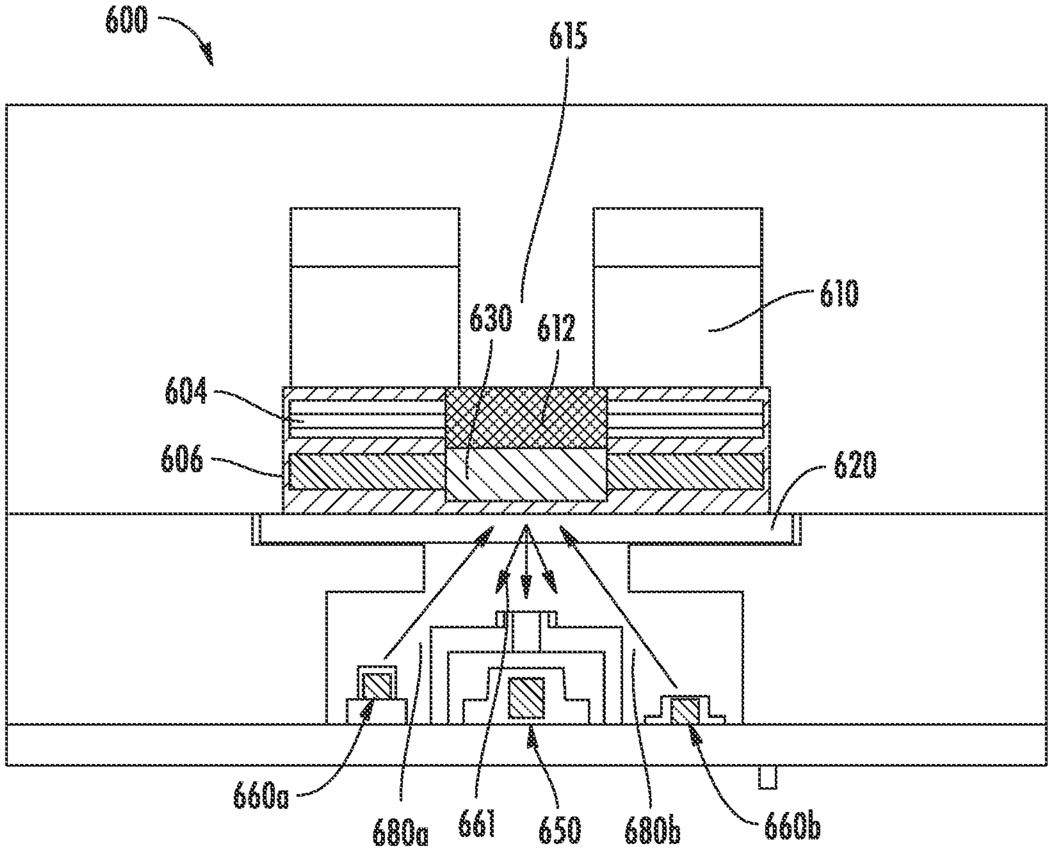
FIG. 6B shows a transverse cross sectional view of the assay reader with an inserted cartridge according to one embodiment of the disclosure.

FIG. 6B shows a schematic illustration of the operation of the assay reader described in FIG. 6A. In FIG. 6B, a cartridge including metering stack 604 and assay stack 606 are inserted into cartridge receiving chamber 610 of assay reader 600. Tab 615 compresses metering stack 604 and assay stack 606 against support surface 620 to cause the fluid sample (e.g., blood fluid sample) to flow from the channel 612 into detection membrane 630. As noted previously, assay reader 600 may be fitted with sensors to confirm that the cartridge has been inserted correctly and in a timely manner. Assay reader 600 may also be pre-programmed before sample collection, either by the user or during the manufacturing process, to illuminate the detection membranes at the appropriate time based on the type of cartridge being used. In this way, assay reader 600 collects assay data from detection membrane 630 only when the assay is completed. Alternatively, if desired, assay reader 600 may be configured to collect assay data from detection membrane 630 during the entire assay reaction after the cartridge has been inserted. As shown in FIG. 6B, light source 660*a*, provides light beam 680*a*, which impinges on the bottom face of detection membrane 630 to produce reflected light beam 661. Similarly, light source 660*b* produces light beam 680*b*, which may impinge on the bottom of the detection membrane 630 to produce reflected light beam 661 at the same time as light source 660*a* or a different time, depending on the requirements of the assays being detected.

Figure 7:
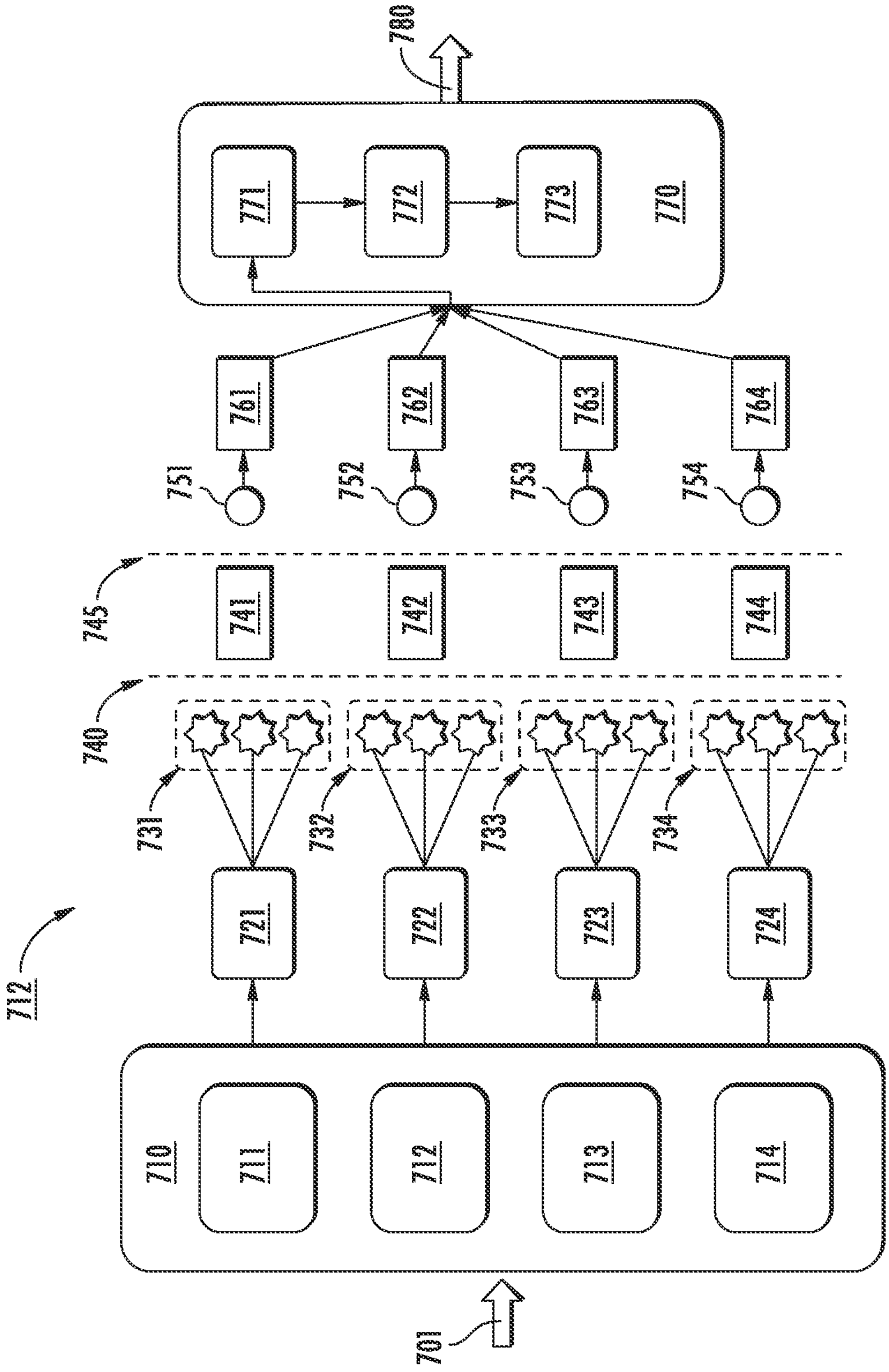
FIG. 7 shows a block diagram of the sensor system of the assay reader, according to an exemplary implementation of the disclosure.

FIG. 7 shows a block diagram 700 of a sensor configuration inside an assay reader according to one exemplary embodiment of the present disclosure. In FIG. 7, four detection membranes (identified by reference numerals 741, 742, 743, and 744) have completed their assay reactions with the target analyte, undergone the respective color changes, and are ready for colorimetric analysis. Note that, if desired, this configuration can also be used to collect data from the four detection membranes to monitor the progress of the assay reactions. Input signal 701 from a first microcontroller serial-peripheral interface bus (MCU SPI Bus) enters digital-to-analog converter unit 710, which includes individual digital-to-analog converters 711, 712, 713, and 714 that independently control current sources 721, 722, 723, and 724. These current sources, in turn, power light sources 731, 732, 733, and 734, respectively. In some embodiments, input signal 701 may be sent by a timing circuit at a predetermined time after the insertion of the cartridge into the assay reader. In such embodiments, the predetermined time corresponds to the known time or times for the assay reactions in the detection membranes to reach completion. In some preferred embodiments, the light sources 731, 732, 733, and 734 are activated at the same time to measure the assay-induced color change of detection membranes 741, 742, 743, and 744 simultaneously in a multiplexed mode via reflectance spectroscopy. However, this present disclosure also contemplates operating all of the light sources separately and sequentially, or some simultaneously and some separately, depending on the timing requirements of the assays in the cartridge.

In this non-limiting example, each of light sources 731, 732, 733, and 734 includes individual three light emitting diodes (LEDs) which may be the same or different colors, depending on the requirements of the assay and any optical elements that may be present in the assay reader. For example, in certain embodiments, the three LEDs in a particular light source (e.g., 731) may be red, green, and blue (RGB LEDs), such that the light impinging on the detection membrane is white light when all three LEDS are activated. Of course, the light sources are not limited to any particular number or type of LEDs or other light generating devices. More generally, the light sources that are useful in the assay readers of the present disclosure are not particularly limited, so long as they provide light of suitable wavelength(s) and brightness for the light detection element to make an accurate reading of the colored light reflected from the detection membrane via reflectance spectroscopy. In certain non-limiting embodiments, the light sources are light emitting diodes (LEDs), organic light emitting diodes (OLEDs), active matrix organic light emitting diodes (AMOLEDs), or lasers. For example, the light source may be only one LED that has sufficient brightness and the proper wavelength to allow colorimetric analysis of an assay reaction in a given detection membrane. In certain embodiments, the light sources may produce light of specific wavelengths. Alternatively, the light source may be a broadband source that is paired with one or more narrow bandpass filters to select light of certain desired wavelength(s). Typically, the light sources produce light in the visible region of the electromagnetic spectrum (i.e., wavelength between 400-700 nm, such as between 500 nm and 550 nm for detecting the concentration of hemoglobin specifically) although this present disclosure also contemplates light sources that produce electromagnetic radiation in the infrared (700 nm to $10^6$ nm) or ultraviolet regions (10 nm-400 nm) of the electromagnetic spectrum, so long as they are paired with the appropriate light detection devices and depending on any additional analytes to be detected. Combinations of different light sources are also expressly contemplated by the present disclosure.

In FIG. 7, element 740 is a schematic representation of optical elements that optionally may be present in the optical path between the light sources 731, 732, 733, and 734 and detection membranes 741, 742, 743, and 744. When desired, one or more optical elements may be located between the light source and its corresponding detection membrane to direct the light, focus the light, reduce undesirable scattering, select one or more wavelengths for assay detection, or some combination thereof. Non-limiting examples of such optical elements include apertures, lenses, light guides, bandpass filters, optical fibers, shutters, and the like. Similarly, element 745 represent optical elements that optionally may be present in the optical path between detection membranes 741, 742, 743, and 744 and corresponding light detection devices 751, 752, 753, and 754. These optical elements may be used to manipulate the light upstream of the light detector devices in a manner similar to that described for element 740. It is to be understood that different types and numbers of optical elements may be used for each combination of light source, detection membrane, and light detection device. Light detecting devices 751, 752, 753, and 754 detect the light from the detection membranes 741, 742, 743, and 744. In this non-limiting example, the light detecting devices are photodiodes. More generally, the type of light detection device is not particularly limited, provided that it is capable of detecting the light that is reflected from the detection membranes used for colorimetric measurement of the assay results. Other examples of suitable light detection elements include photodiode arrays, CCD chips, and CMOS chips. The outputs from light detection devices (e.g., photodiodes) 751, 752, 753, and 754 are sent to transimpedance amplifier/low pass filter elements 761, 762, 763, and 764, which convert the current signal from the photodiodes to a voltage output, while filtering unwanted signal components. The output from transimpedance amplifier/low pass filter elements 761, 762, 763, and 764 are sent to analog-to-digital converter unit 770, which includes multiplexer unit 771, gain 772, and analog-to-digital converter 773. The output of analog-to-digital converter unit 770 may be sent to a component 780, which may be a second MCU SPI bus, a transmitter, or a processor. In certain embodiments, the transmitter allows for hardwired or wireless connectivity (e.g., Bluetooth or Wi-Fi) with a personal computer, mobile device, or computer network. In one particularly useful embodiment, the assay results are transmitted to the user's mobile device or personal computer, where they are displayed in a graphical user interface (GUI). If desired, the GUI may display prior assay results, in addition to the current results, in order to provide the user with information regarding the overall trends in the results of the assays. In addition, the assay results may be transmitted from the user's mobile device or computer to a computer network, such as one belonging to the user's physician. In this way, the assay systems of the present disclosure can allow a user's physician to monitor a patient closely, by providing up-to-date medical information from the assay results obtained by the assay reader.

It should be noted that the optical detection systems described in the foregoing correspond to some exemplary embodiments of the system, but that the present disclosure expressly contemplates other types of detection systems as well. In general, any detection system which corresponds to a signal change caused by an assay reaction may be used in connection with the assay reader of the present disclosure. Thus, for example, in certain embodiments, the detection system is an optical detection system that is based on chemiluminescence. In such embodiments, light sources such as LEDS and OLEDS are not required to detect a color change caused by the assay reaction in the detection membranes, Rather, the signal chance may be caused by the reaction of an oxidative enzyme, such as luciferase, with a substrate which results in light being generated by a bioluminescent reaction. In another exemplary embodiment, the signal change caused by the assay reaction may be detected by electrochemical reaction.

FIGS. 8A-8D illustrate a further embodiment of cartridges 100, 200, or 502 in the form of a cartridge 800 that includes a metering stack 802 and an assay stack 804 during various stages of performing an assay after a blood fluid sample 814 containing hemoglobin 816 trapped inside red blood cells 822, inter glia, has been introduced to the cartridge 800. The metering stack 802 is configured to receive and distribute the blood fluid sample 814 along a channel, where the channel has one or more venting holes in communication with the channel, as described in detail above. As also described above, a spacer material may be disposed between the metering stack and the assay stack, wherein the spacer material provides a gap between the metering stack and the assay stack that prevents the target analyte from flowing from the metering stack into the assay stack when the cartridge is in an uncompressed state. Additionally, the blood fluid sample 814 can flow from the metering stack 802 to the assay stack 804 upon compression of the cartridge 800.

Once introduced to the metering stack 802 at an upstream location U, the blood fluid sample 814 passes to an upstream side 832 of a separation membrane 806 also having a downstream side 833, and ultimately, the target analyte (e.g., hemoglobin 816) reaches an upstream side 845 of a detection membrane 812 (e.g., a color generation membrane) of the assay stack 804, where the detection membrane 812 also has a downstream side 846 as discussed in more detail below. It should be understood the separation membrane 806 can be referred to as the plasma separation membrane, where the separation membrane 806 allows for the separation of red blood cells 822 from the blood fluid sample while allowing for a target analyte (e.g., hemoglobin 816) to pass through the separation membrane 806 to the detection membrane 812. The separation membrane 806 can be formed from one or more hydrophobic polymers, such as a sulfone polymer, a mixed cellulose ester, or a combination thereof. The sulfone polymer can be a polysulfone, a polyethersulfone, a polyarylsulfone, or a combination thereof. In some instances, the hydrophobic polymers described above can be reacted with or mixed with a hydrophilic polymer (e.g., polyvinylpyrrolidone or PVP) for use in applications involving aqueous environments. For example, the separation membrane 806 can include a sulfone polymer cross linked with polyvinylpyrrolidone.

Further, the separation membrane 806 can include a first plurality of pores 834 located towards the upstream side 832 of the separation membrane 806 and a second plurality of pores 836 located towards the downstream side 833 of the separation membrane 806. The first plurality of pores 834 have an average pore size that is larger than an average pore size of the second plurality of pores 836. For instance, the first plurality of pores 834 in the separation membrane 806 can have an average pore size ranging from about 10 micrometers to about 150 micrometers, such as from about 15 micrometers to about 125 micrometers, such as from about 20 micrometers to about 100 micrometers, while the second plurality of pores 836 in the separation membrane 806 can have an average pore size ranging from about 0.1 micrometers to about 7.5 micrometers, such as from about 0.5 micrometers to about 5 micrometers, such as from about 1 micrometer to about 2.5 micrometers. A separation membrane 806 having such a pore size arrangement and distribution can be referred to as asymmetric, and the ratio of the average pore size of the first plurality of pores 834 to the average pore size of the second plurality of pores 836 can range from about 1.3 to about 1500. Thus, the separation membrane 806 has pore sizes that are large enough to allow the hemoglobin 816 to pass through to the detection membrane 812 but that also have a pore size small enough to prevent the passage of any intact red blood cells 822, which have a diameter of greater than about 7 micrometers to 9 micrometers, to the detection membrane 812, which could affect the accuracy of the assay results.

Figure 8A:
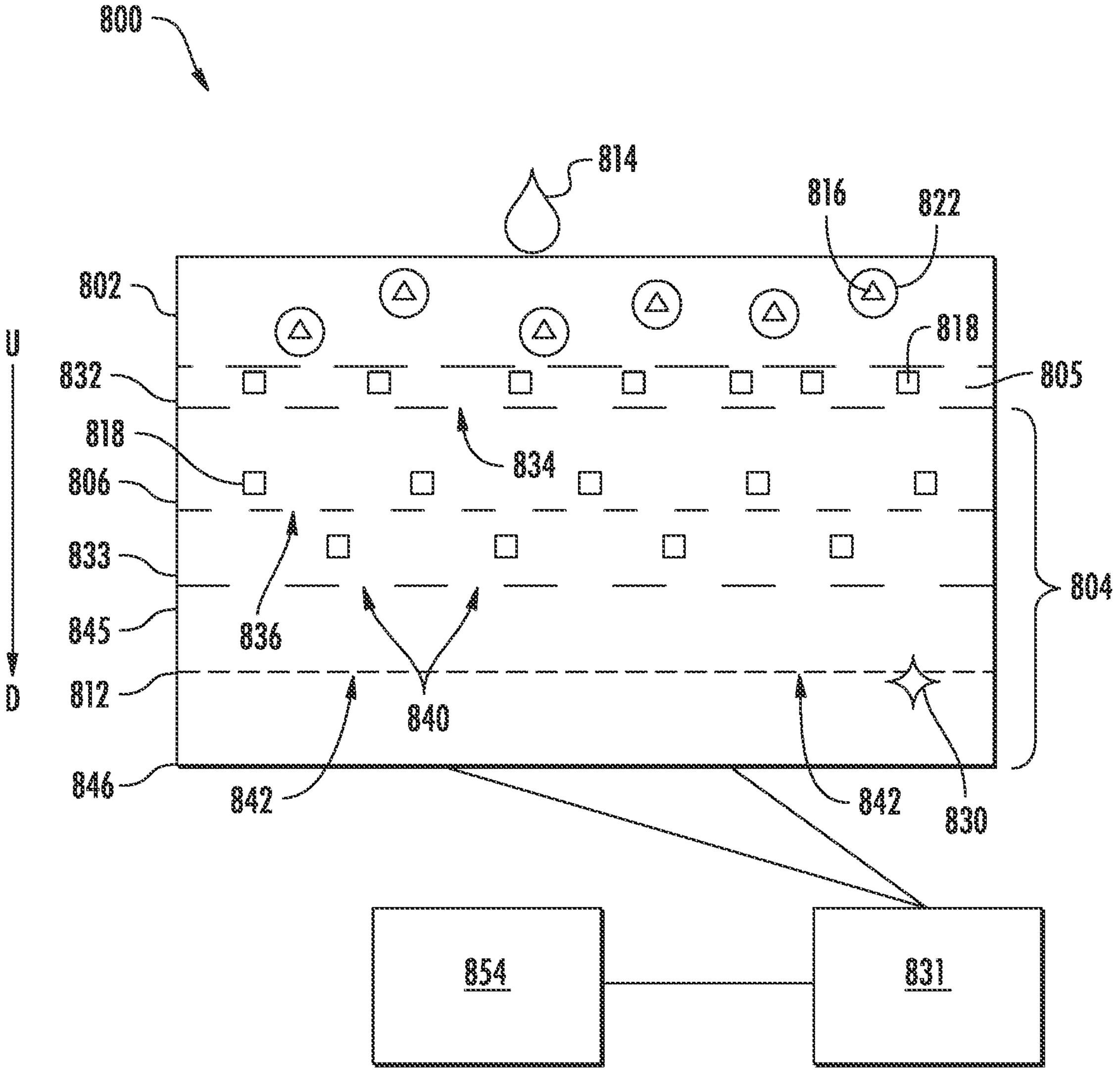
FIGS. 8A-8D illustrate a cartridge that includes a metering stack and an assay stack during various stages of the assay process after a blood fluid sample has been introduced to the cartridge.

Additionally, as shown in FIG. 8A and as mentioned above, the separation membrane 806 includes a cell lysing reagent 818 for lysing the red blood cells 822 to release the hemoglobin 816 so that it can pass to the detection membrane 812 at a downstream location D. In some embodiments, the cell lysing reagent 818 includes a detergent. For instance, the cell lysing reagent 818 can include an anionic detergent such as but not limited sodium dodecyl sulfate (also referred to as sodium lauryl sulfate), a cationic detergent such as but not limited to ethyl trimethyl ammonium bromide, or a nonionic detergent such as polyoxyethylene sorbitol ester (Tween or polysorbate), octyl glucoside, or octyl thioglucoside. Further, the cell lysing reagent 818 can be present in the separation membrane 806 at a concentration greater than 0.75 wt. % (7.5 milligrams per milliliter) and less than 2.5 wt. % (25 milligrams/milliliter), such as from about 0.8 wt % (8 milligrams/milliliter) to about 2.25) wt. % (22.5 milligrams/milliliter), such as from about 0.9 wt % (9 milligrams/milliliter) to about 2 wt. % (20 milligrams/milliliter), such as from about 0.95 wt. % (9.5 milligrams/milliliter) to about 1.75 wt. % (17.5 milligrams/milliliter) based on the wet weight of the cell lysing reagent 818 present on the separation membrane 806. Further, once dried, the cell lysing reagent 818 can be present on the separation membrane 806 in an amount greater than 200 micrograms/square centimeter to less than 675 micrograms/square centimeter, such as from about 225 micrograms/square centimeter to about 500 micrograms/square centimeter, such as from about 250 micrograms/square centimeter to about 300 micrograms/square centimeter based on the dry weight of the cell lysing reagent 818 on the separation membrane 806. Although any suitable solvent or buffer solution can be used, in one embodiment, the cell Rising reagent is dissolved in deionized water prior to coating the resulting solution onto the separation membrane 806.

Figure 8B:
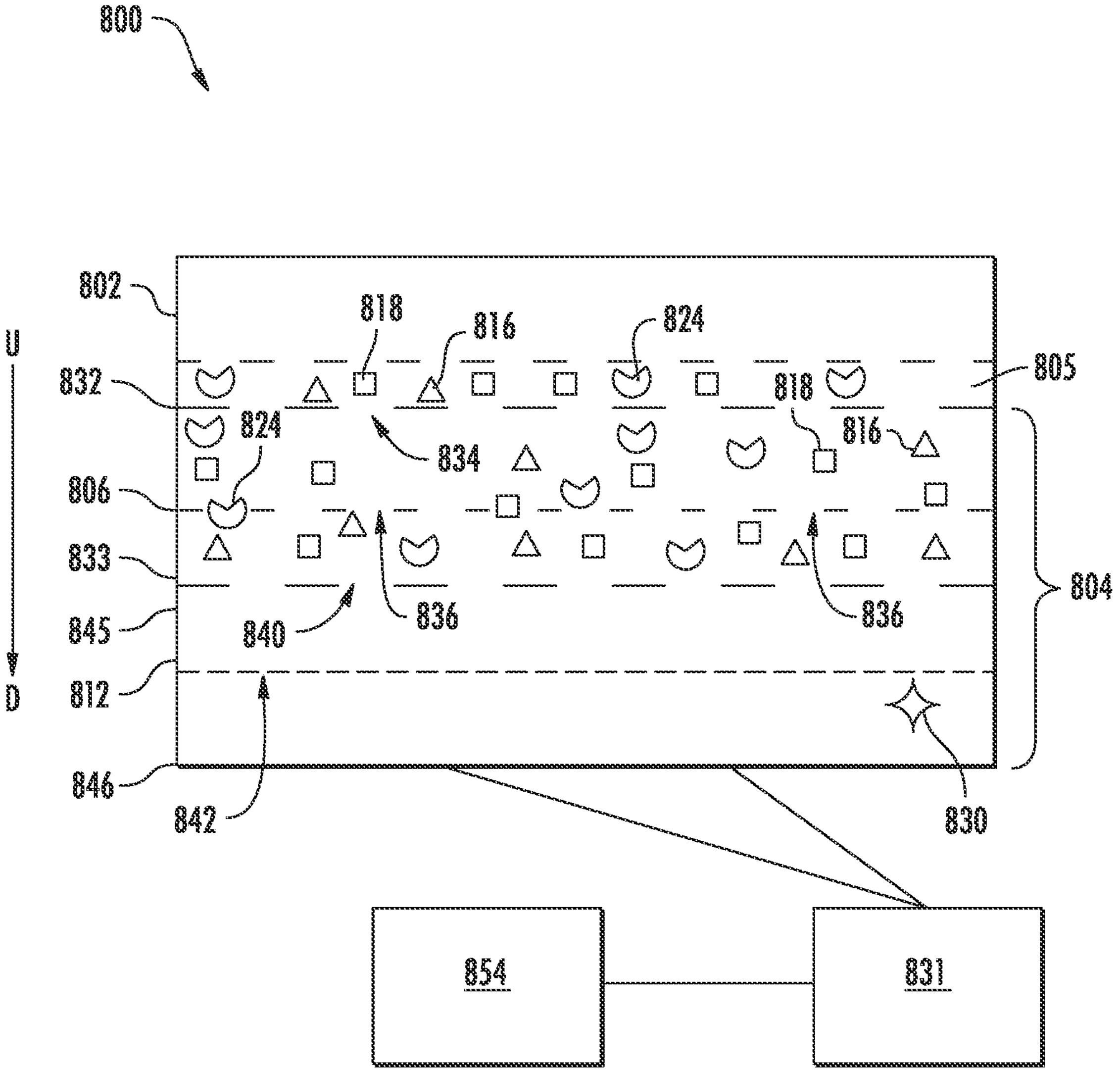
Figure 8C:
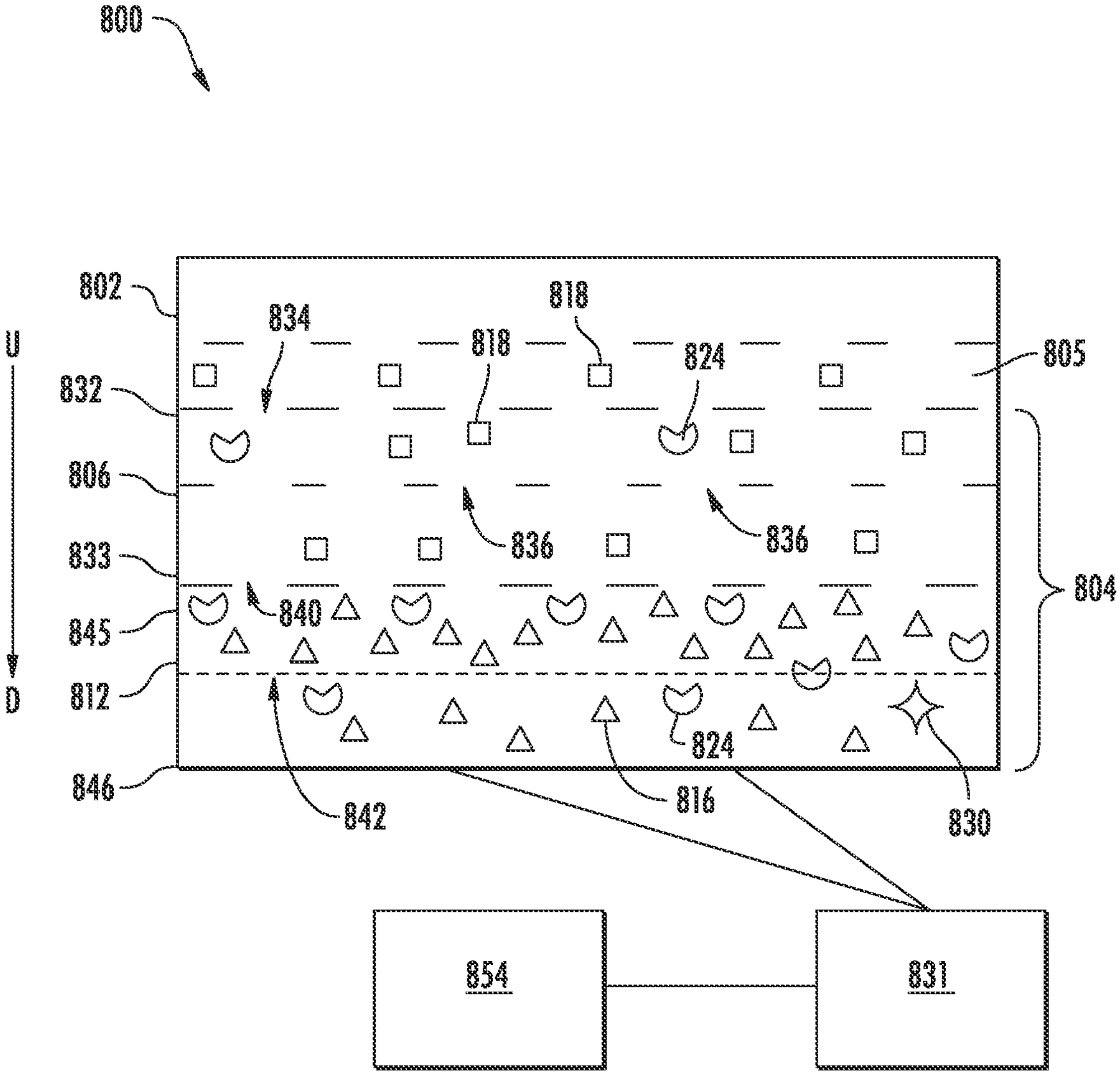

Ultimately, as shown in FIGS. 8B and 8C, any red blood cells 822 present in the blood fluid sample 814 can be lysed or burst by the cell lysing reagent 818 present on the separation membrane 806 and the released hemoglobin 816 can pass through the separation membrane 806 to the detection membrane 812. As shown, other components of the lysed red blood cells 824 present in the blood fluid sample 814 may also pass to the detection membrane 812 but do not interfere with the measurement of hemoglobin 816 present in the blood fluid sample 814.

Further, as shown in FIGS. 8A-8D, it should be understood that the cell lysing reagent 818 can alternatively or additionally be present on a mesh layer 805 positioned upstream of the separation membrane 806 that forms part of assay stack 804. Specifically, the porous or mesh layer 805 can be coated with the cell lysing reagent 818 in the same manner in which it is applied to the separation membrane 806. In some embodiments, only the mesh layer 805 is coated with the cell lysing reagent 818, while in other embodiments, both the mesh layer 805 and the separation membrane 806 are both coated with the cell lysing reagent 818. In still other embodiments, only the separation membrane 806 is coated with the cell lysing reagent 818.

The detection membrane can be formed from one or more hydrophobic polymers, such as a sulfone polymer, a mixed cellulose ester, or a combination thereof. The sulfone polymer can be a polysulfone, a polyethersulfone, a polyarylsulfone, or a combination thereof. In some instances, the hydrophobic polymers described above can be reacted with or mixed with a hydrophilic polymer (e.g., polyvinylpyrrolidone or PVP) for use in applications involving aqueous environments. For example, the detection membrane 812 can include a sulfone polymer cross linked with polyvinylpyrrolidone. Further, the detection membrane 812 can include a first plurality of pores 840 located towards the upstream side 845 of the detection membrane 812 and a second plurality of pores 842 located towards the downstream side 846 of the detection membrane 812. The first plurality of pores 840 have an average pore size that is larger than an average pore size of the second plurality of pores 842. For instance, the first plurality of pores 834 in the detection membrane 812 can have an average pore size ranging from about 5 micrometers to about 150 micrometers, such as from about 7.5 micrometers to about 125 micrometers, such as from about 10 micrometers to about 100 micrometers, while the second plurality of pore 836 in the detection membrane 812 can have an average pore size ranging from about 0.05 micrometers to about 0.3 micrometers, such as from about 0.075 micrometers to about 0.25 micrometers, such as from about 0.1 micrometers to about 0.2 micrometers. A detection membrane 812 having such a pore size arrangement and distribution can be referred to as asymmetric, and the ratio of the average pore size of the first plurality of pores 840 to the average pore size of the second plurality of pores 842 can range from about 25 to about 3000. Thus, the detection membrane 812 has pore sizes that are large enough on the upstream side 845 to allow the hemoglobin 816 to pass through to the detection membrane 812 but that also have a pore size small enough, particularly on the downstream side 846, to enhance the sensitivity of the assay by controlling the flow of the hemoglobin 816 to improve the accuracy of the hemoglobin concentration assay results.

Figure 8D:
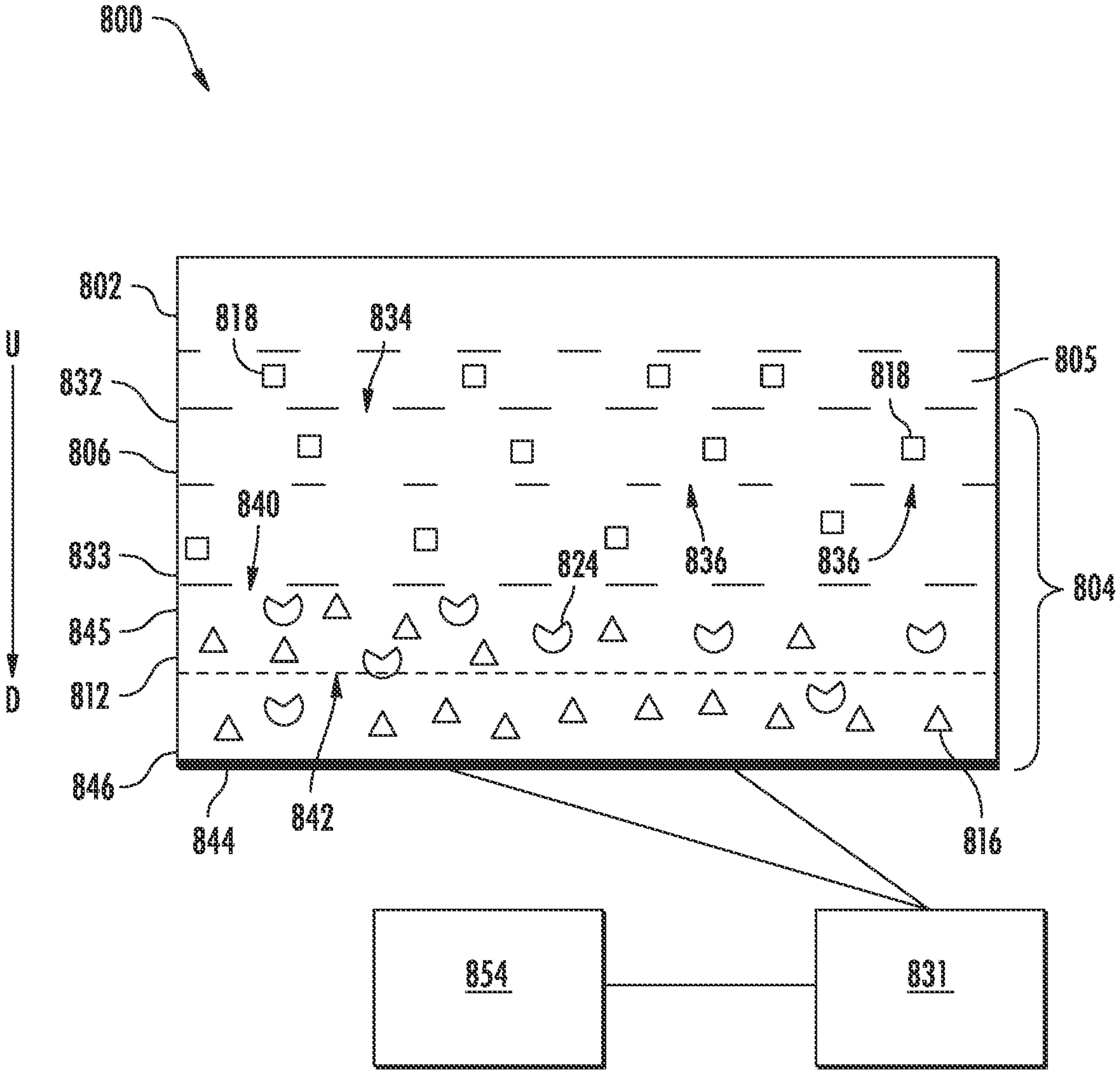

Turning now to FIGS. 8C-8D, after the hemoglobin 816 passes from the upstream side U of the cartridge 800 to the downstream side D of the cartridge 800 through various pores in the separation membrane 806, the hemoglobin 816 can pass through to the detection membrane 812. Although not required, the detection membrane 812 can include any suitable hemoglobin detection reagent 830 known by one of skill in the art that can react with hemoglobin 816 present can elicit a quantifiable response 844 (e.g., a colorimetric response, a fluorescent response, an electrochemical response, etc.) in the presence of the hemoglobin 816, wherein the quantifiable response 844 corresponds to an amount of the hemoglobin 816 present in the detection membrane 812 as shown in FIGS. 8C and 8D.

In any event and whether a hemoglobin detection reagent 830 is utilized or not, the quantifiable response 844 (e.g., a colorimetric response, a fluorescent response, an electrochemical response, etc.) in the detection membrane 812 can be detected by one or more detection devices, which, for example, can include light detection devices 854 as shown in FIG. 8D when the quantifiable response is a color change. Meanwhile, one or more light sources 831 provide light for detecting the quantifiable response 844 (e.g., color change) in the detection membrane 812 (e.g., color generation membrane) and can be positioned near light detection device 864. In the case of a colorimetric response, the one or more light sources 831 provide light to analyze the quantifiable response 844 (e.g., color change) in the detection membrane 812 (e.g., color generation membrane) corresponding to light detection device 854. As described above, it is advantageous to dedicate one or more light sources to each light detection element in order to ensure that the photon flux onto the light detection element is sufficient to obtain an accurate reading. In some embodiments, the light sources 831 dedicated to a particular light detection device 854 have the same output spectrum. In other embodiments, however, the light sources 831 corresponding to a given light detection devices 854 produce different output spectra. Fax instance, the light sources may be light emitting diodes (LEDs) that produce different colors of light. In general, it is advantageous to include optical elements to direct the light and/or reduce the amount of light scattering in the assay reader. If desired, the light detection device 854 may be fitted with a filter to admit only light of a predetermined wavelength or wavelength range for detection by light detection device 854. This may be useful, for example, when the light sources 831 are equipped to provide only white light for colorimetric analysis. In addition, the light from light sources 831 and the light to be detected by light detection device 854 may be directed or manipulated using optical elements such as lenses, filters, shutters, fiber optics, light guides, and the like without departing from the spirit and the scope of the present disclosure. More generally, the light sources 831 that are useful in the assay readers of the present disclosure are not particularly limited, so long as they provide light of suitable wavelength(s) and brightness for the light detection devices 854 to make an accurate reading of the colored light reflected from the detection membrane 812 via reflectance spectroscopy.

It should also be understood that the detection membrane 812 can include one or more stabilizing agents (not shown). Such stabilizing agents can include neo silk protein saver; mannitol, trehalose, or other sugars; polypropylene glycol-polyethylene glycol block copolymers or other hydrophilic-hydrophobic block copolymers; or a combination thereof.

Figure 9:
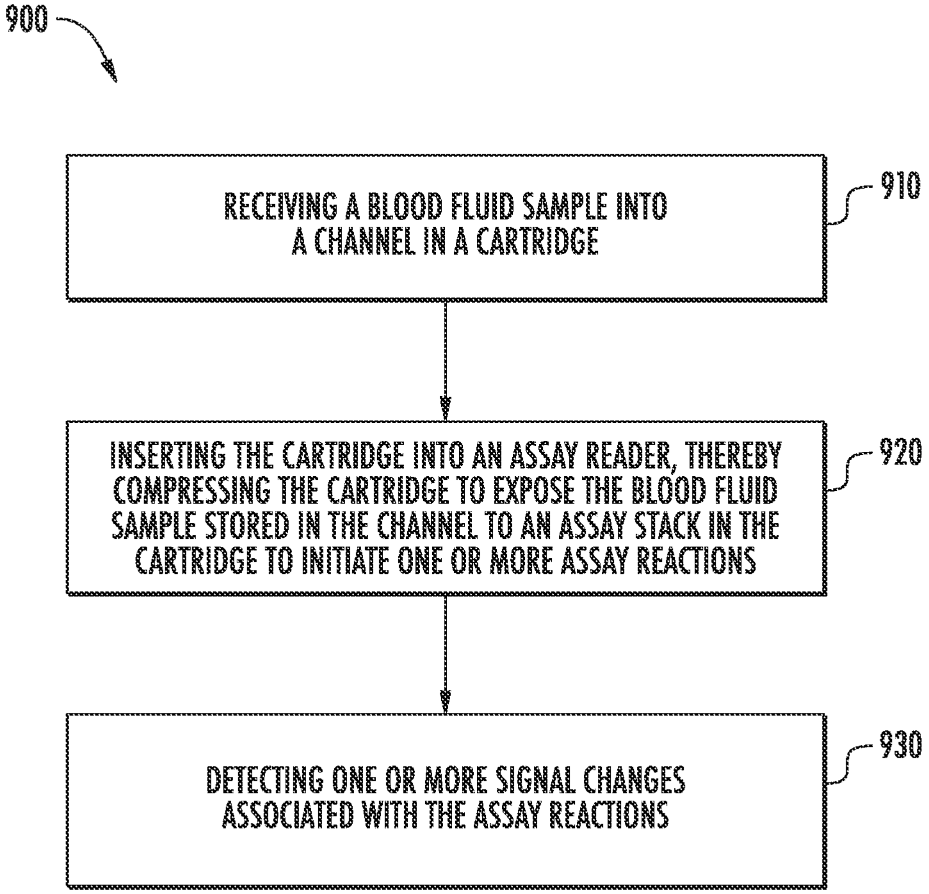
FIG. 9 shows a flow chart illustrating a method of using the assay system according to an exemplary implementation of the disclosure.

FIG. 9 shows a flowchart that illustrates a method 900 of using of the assay system according to one embodiment of the present disclosure to perform a plurality of assays. The method 900 includes step 910, which involves receiving a blood fluid sample that contains the target analyte (e.g., hemoglobin) into a channel in a cartridge. Step 920 involves inserting the cartridge into an assay reader, thereby compressing the cartridge to the blood fluid sample stored in the channel to an assay stack in the cartridge to initiate one or more assay reactions. Step 930 involves detecting one or more signal changes associated with the plurality of assay reactions. The method 900 can include any additional steps that would be understood by one of ordinary skill in the art to detect the one or more signal changes via the various components of the metering stack and assay stack described in detail above.

Figure 10:
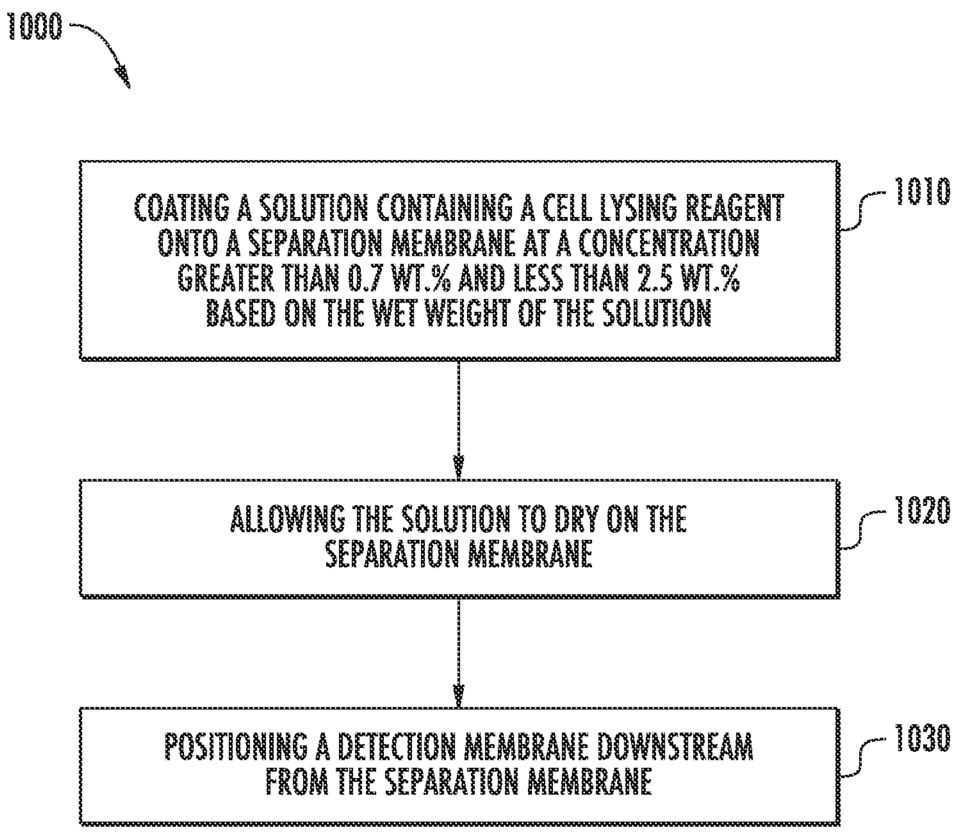
FIG. 10 shows a flow chart illustrating a method of manufacturing a cartridge according to one exemplary implementation of the disclosure.

FIG. 10 shows a flowchart that illustrates a method 1000 of fabricating a cartridge according to one embodiment of the present disclosure. The method includes the steps of obtaining a separation membrane, coating a solution containing a cell lysing reagent onto the separation membrane at a concentration greater than 0.75 wt. % and less than 2.5 wt. % based, on the wet weight of the solution (step 1010). The method 1000 also includes a step of allowing the solution to dry on the separation membrane (step 1020). The method 1000 also includes the step of obtaining a detection membrane and positioning the detection membrane downstream from the separation membrane (step 1030). In utilizing an assay device fabricated by this method, the concentration of hemoglobin in a blood fluid sample can be determined via a vertical flow assay device where the blood fluid sample is applied on an upstream side of the device and the concentration is determined on a downstream side of the device via reflectance spectroscopy.

EXAMPLES

The present disclosure may be better understood by reference to the following examples.

Example 1

Figure 11:
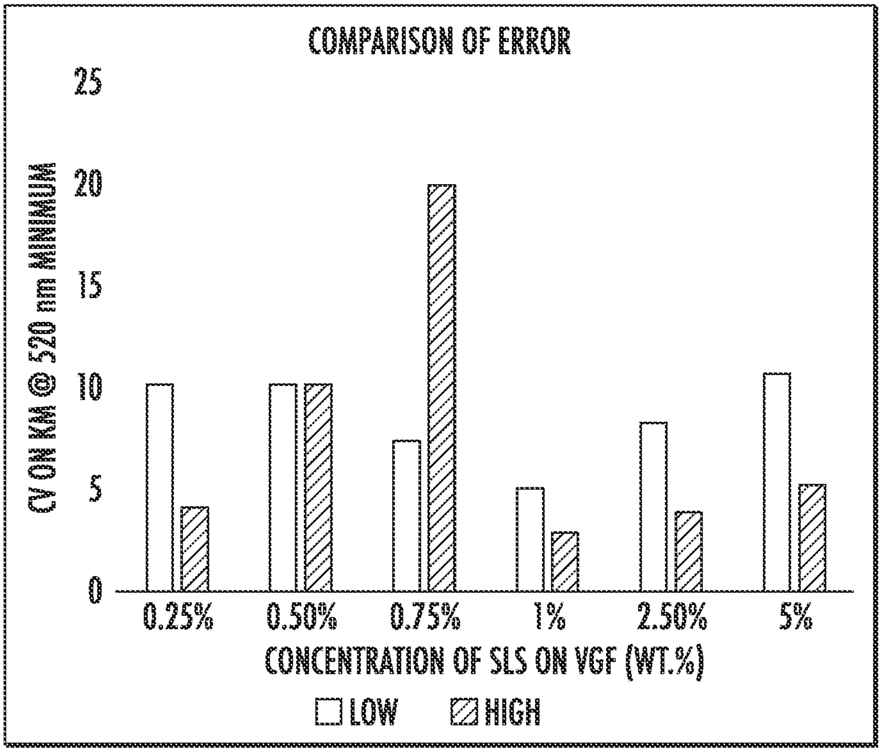
FIG. 11 shows a graph of the coefficient of variation of the signal for measurement of hemoglobin (Kubelka-Munk (KM) transformation from reflectance value) in a detection membrane for fluid samples containing a known low concentration of hemoglobin and a known high concentration of hemoglobin when the separation membrane contained varying concentrations of a cell lysing reagent for releasing the hemoglobin from red blood cells in the fluid sample.

Various concentrations of a cell lysing agent (e.g., sodium lauryl sulfate or sodium dodecyl sulfate (SDS) in solution were applied to a Vivid GF (VGF) asymmetric polysulfone membrane from Pall Corporation, which served as a plasma separation membrane in other embodiments. The concentrations of the sodium lauryl sulfate (SLS) in deionized water applied to the membrane were 0.25 wt. %, 0.50 wt. %, 0.75 wt. %, 1 wt. %, 2.5 wt. %, and 5 wt. %. The coated separation membrane was built into an assay stack atop the detection membrane, which consisted of specifically chosen asymmetric pores, and blood fluid samples containing a known low concentration of hemoglobin and a known high concentration of hemoglobin were applied to the assay stack. Reflectance measurements were then taken from below the detection membrane using an LED at a wavelength of 520 nm. The endpoint reflectance after a 1 minute time period was taken and the Kubelka-Munk transformation was used to obtain a linear regression. The coefficient of variation was determined for each concentration of SLS, at the high and low hemoglobin concentration from the KM values of repeat measurements (FIG. 11). In addition, the slope on linear regression was compared across the various SLS concentrations coated onto the VGF (FIG. 12).

Figure 12:
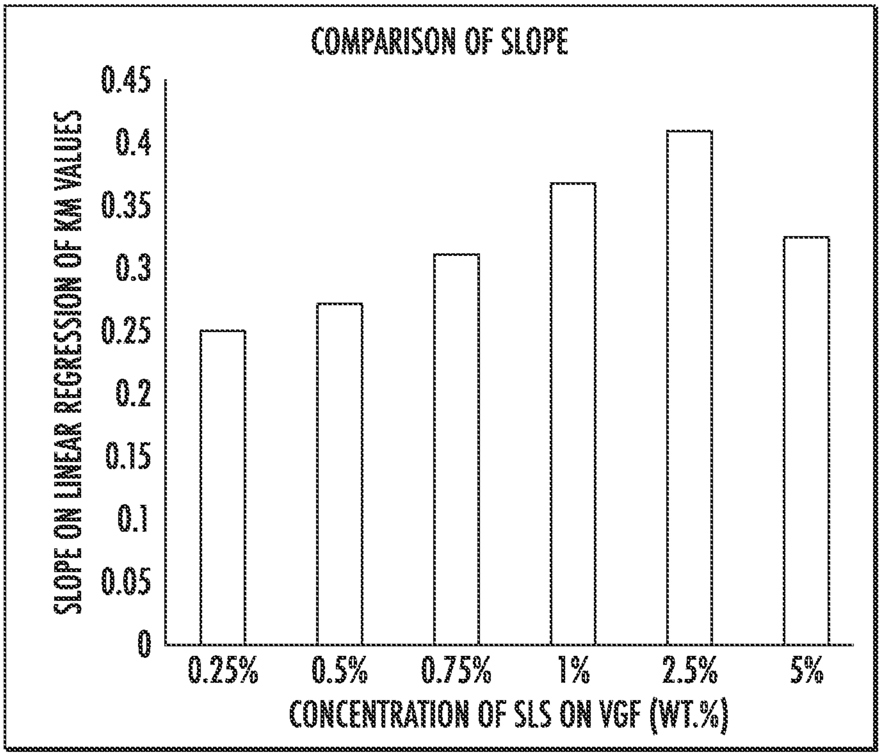
FIG. 12 shows a graph of the linear regression slope of the signal for measurement of hemoglobin (Kubelka-Munk (KM) transformation from reflectance value) in a detection membrane for fluid samples containing a known low concentration of hemoglobin and a known high concentration of hemoglobin when the separation membrane contained varying concentrations of a cell lysing reagent for releasing the hemoglobin from red blood cells in the fluid sample.

As can be seen from a review of FIGS. 11 and 12, at low concentrations of SLS on the coated VGF (e.g., 0.75 wt. % and less) and at high concentrations of SLS on the coated VGF (e.g., greater than 2.5 wt. %), the coefficient of variation (CV) on the KM values were increased for both the low and high concentrations of hemoglobin. Meanwhile, at concentrations greater than 0.75 wt. % and less than 2.5 wt. %, the coefficient of variation was reduced for both the low and high concentrations of hemoglobin, which indicates that a cell lysing reagent concentration that is greater than 0.75 wt. % and less than 2.5 wt. % surprisingly provides for more accurate hemoglobin concentrations than cell lysing reagent concentrations above and below that range. Additionally, when comparing the slope obtained from the linear regression, this increases with increasing SLS concentrations until concentrations greater than 2.5 wt. % when the slope starts to decrease. This suggests that coating concentrations greater than 0.75 wt. % but no greater than 2.5 wt. % are preferable to obtain the most sensitive assay while retaining good precision.

Example 2

Next, two different detection membranes were used to analyze hemoglobin based on reflectance (%) and the Kubelka-Munk (KM) transformation from the reflectance value. The separation membrane (VGF) was coated with 1% SDS and the detection membranes were both asymmetric polysulfone membranes, described in detail above, where one membrane had a downstream pore size of 0.1 micrometers and the other membrane had a downstream pore size of 0.45 micrometers. The membranes were both MMM membranes from Pall Corporation. The results are shown in FIGS. 13-14.

Figure 13:
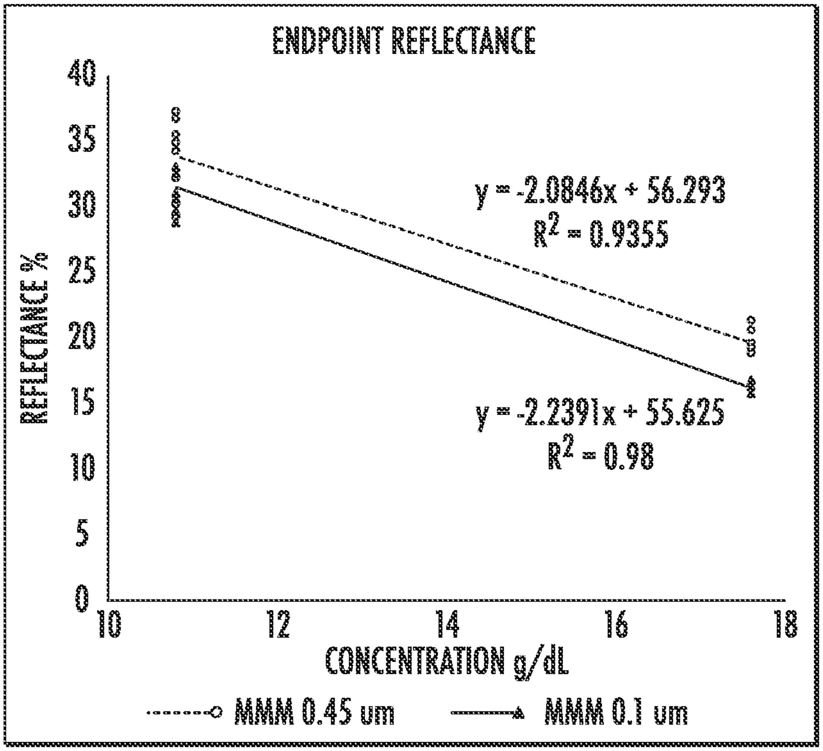
FIG. 13 shows a graph of the reflectance measurements for various concentrations of hemoglobin in blood fluid samples when the detection membrane had a pore size of 0.45 micrometers or 0.1 micrometers.
Figure 14:
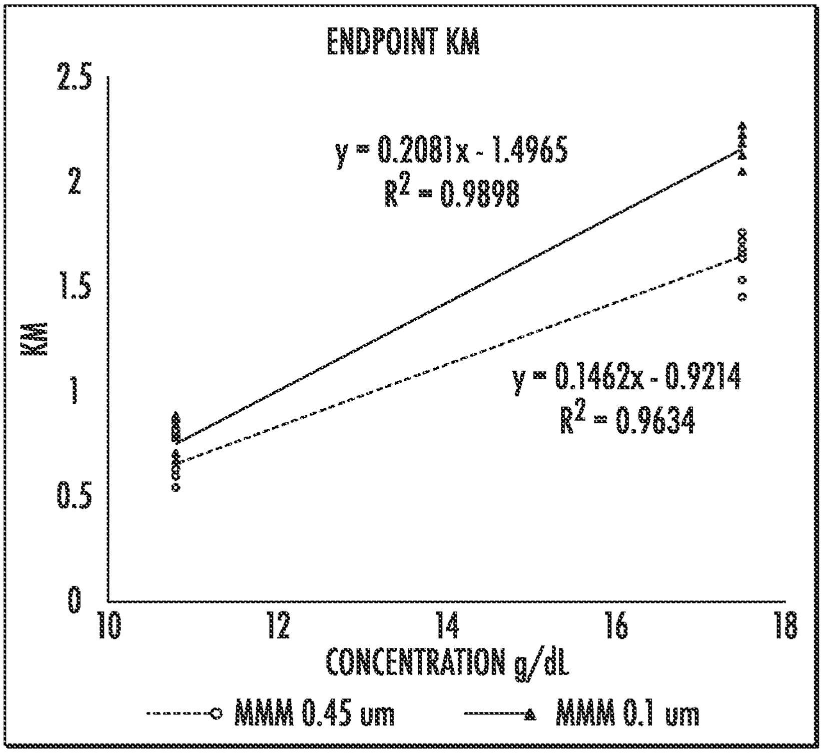
FIG. 14 shows a graph of the signal for measurement of hemoglobin (Kubelka-Munk (KM) transformation from reflectance value) for various concentrations of hemoglobin in blood fluid samples when the detection membrane had a pore size of 0.45 micrometers or 0.1 micrometers.

FIG. 13 shows a graph of the endpoint reflectance measurements (%) for various concentrations of hemoglobin in blood fluid samples when the detection membrane had a pore size of 0.45 micrometers or 0.1 micrometers, while FIG. 14 shows a graph of the signal for measurement of hemoglobin (Kubelka-Munk transformation from reflectance value or KM) for various concentrations of hemoglobin in blood fluid samples when the detection membrane had a pore size of 0.45 micrometers or 0.1 micrometers. FIGS. 13-14 show that the slope and thus the sensitivity of the hemoglobin assay of the present disclosure is improved when the downstream pore size of the detection membrane is 0.1 micrometers compared to when the downstream pores size of the detection membrane is 0.45 micrometers across hemoglobin concentrations ranging from about 11 g/dL to about 18 g/dL.

While various embodiments of the present disclosure have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment, Thus, the breadth and scope of the present disclosure should not be limited by any of the above-described exemplary embodiments.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' containing; or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the present disclosure, but instead as merely intended to highlight alternative or additional features that may or may not be utilized in a particular embodiment of the present disclosure. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations, in addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone. A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone. A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. An assay device for determining a concentration of hemoglobin in a blood fluid sample, wherein the assay device comprises:

a separation membrane, wherein the separation membrane contains a cell lysing reagent, wherein the cell lysing reagent is present on the separation membrane in an amount greater than 200 micrograms/square centimeter to less than 675 micrograms/square centimeter based on the dry weight of the cell lysing reagent on the separation membrane; and a detection membrane located downstream from the separation membrane and configured to elicit a quantifiable response in the presence of hemoglobin in the blood fluid sample, wherein the quantifiable response corresponds to an amount of hemoglobin present in the blood fluid sample, wherein the detection membrane is asymmetric and has a first plurality of pores located towards an upstream side of the detection membrane and a second plurality of pores located towards a downstream side of the detection membrane, wherein the first plurality of pores have an average pore size that is larger than an average pore size of the second plurality of pores.

2. The assay device according to claim 1, wherein the assay device is a vertical flow assay device.

3. The assay device according to claim 1, wherein the assay device determines a concentration of one or more analytes in addition to determining the concentration of hemoglobin in the blood fluid sample.

4. The assay device according to claim 1, wherein the quantifiable response is measurable from the downstream side of the detection membrane.

5. The assay device according to claim 1, wherein the quantifiable response is measurable via reflectance spectroscopy.

6. The assay device according to claim 1, wherein the cell lysing reagent comprises a detergent.

7. The assay device according to claim 1, wherein the separation membrane is asymmetric and has a first plurality of pores located towards an upstream side of the separation membrane and a second plurality of pores located towards a downstream side of the separation membrane, wherein the first plurality of pores have an average pore size that is larger than an average pore size of the second plurality of pores.

8. The assay device according to claim 7, wherein the first plurality of pores in the separation membrane have an average pore size ranging from about 10 micrometers to about 150 micrometers and the second plurality of pores in the separation membrane have an average pore size ranging from about 0.1 micrometers to about 7.5 micrometers.

9. The assay device according to claim 1, wherein the first plurality of pores in the detection membrane have an average pore size ranging from about 5 micrometers to about 150 micrometers and the second plurality of pores in the separation membrane have an average pore size ranging from about 0.05 micrometers to about 0.3 micrometers.

10. The assay device according to claim 1, wherein the separation membrane, the detection membrane, or both comprises a hydrophobic polymer.

11. The assay device according to claim 10, wherein the separation membrane, the detection membrane, or both comprises a sulfone polymer, a mixed cellulose ester, or a combination thereof.

12. A method of fabricating an assay device for determining a concentration of hemoglobin in a blood fluid sample, the method comprising:

coating a solution containing a cell lysing reagent onto to a separation membrane, wherein the cell lysing reagent is present on the separation membrane in an amount greater than 200 micrograms/square centimeter to less than 675 micrograms/square centimeter based on the dry weight of the cell lysing reagent on the separation membrane after the solution has dried on the separation membrane;

allowing the solution to dry on the separation membrane; and positioning a detection membrane downstream from the separation membrane, wherein the detection membrane is configured to elicit a quantifiable response in the presence of hemoglobin in the blood fluid sample, wherein the quantifiable response corresponds to an amount of hemoglobin present in the blood fluid sample, wherein the detection membrane is asymmetric and has a first plurality of pores located towards an upstream side of the detection membrane and a second plurality of pores located towards a downstream side of the detection membrane, wherein the first plurality of pores have an average pore size that is larger than an average pore size of the second plurality of pores.

13. The method according to claim 12, wherein the quantifiable response is measurable from the downstream side of the detection membrane and/or is measurable via reflectance spectroscopy.

14. The method according to claim 12, wherein the cell lysing reagent comprises a detergent.

15. The method according to claim 12, wherein the separation membrane is asymmetric membrane and has a first plurality of pores located towards an upstream side of the separation membrane and a second plurality of pores located towards a downstream side of the separation membrane, wherein the first plurality of pores have an average pore size that is larger than an average pore size of the second plurality of pores.

16. The method according to claim 15, wherein the first plurality of pores in the separation membrane have an average pore size ranging from about 10 micrometers to about 150 micrometers and the second plurality of pores in the separation membrane have an average pore size ranging from about 0.1 micrometers to about 7.5 micrometers.

17. The method according to claim 12, wherein the first plurality of pores in the detection membrane have an average pore size ranging from about 5 micrometers to about 150 micrometers and the second plurality of pores in the separation membrane have an average pore size ranging from about 0.05 micrometers to about 0.3 micrometers.

18. The method according to claim 12, wherein the separation membrane, the detection membrane, or both comprises a hydrophobic polymer.

19. The method according to claim 18, wherein the separation membrane, the detection membrane, or both comprises a sulfone polymer, a mixed cellulose ester, or a combination thereof.

20. The method according to claim 12, wherein the cell lysing reagent is present in the solution in an amount greater than 0.75 wt. % and less than 2.5 wt. % based on the wet weight of the solution.

* * * * *